(12) United States Patent
Zama et al.

(10) Patent No.: US 8,105,803 B2
(45) Date of Patent: Jan. 31, 2012

(54) PHOSPHATASES INVOLVED IN THE REGULATION OF CARDIOMYOCYTE DIFFERENTIATION

(75) Inventors: Takeru Zama, Tokyo (JP); Mitsuru Murata, Tokyo (JP); Yasuo Ikeda, Tokyo (JP)

(73) Assignee: Keio University, Tokyo (JP)

( * ) Notice: Subject to any disclaimer, the term of this patent is extended or adjusted under 35 U.S.C. 154(b) by 401 days.

(21) Appl. No.: 12/296,407

(22) PCT Filed: Apr. 12, 2007

(86) PCT No.: PCT/JP2007/058079
§ 371 (c)(1),
(2), (4) Date: Jan. 14, 2009

(87) PCT Pub. No.: WO2007/119787
PCT Pub. Date: Oct. 25, 2007

(65) Prior Publication Data
US 2009/0291439 A1    Nov. 26, 2009

(30) Foreign Application Priority Data
Apr. 14, 2006   (JP) .................................. 2006-112524

(51) Int. Cl.
*C12P 21/06*   (2006.01)
*C07K 14/00*   (2006.01)

(52) U.S. Cl. ......................................... 435/69.1; 514/1
(58) Field of Classification Search ...... 514/1; 435/69.1
See application file for complete search history.

(56) References Cited

FOREIGN PATENT DOCUMENTS
WO   WO0060098   * 10/2000

OTHER PUBLICATIONS www.ncbi.nlm.nih.gov/protein/68344571;2011.*
Translation of International Preliminary Report on Patentability for International Application PCT/JP2007/058079, mailed Nov. 27, 2008.
Nakamura et al., "Molecular Cloning and Characterization of a Novel Dual-Specificity Protein Phosphatase Possibly Involved in Spermatogenesis," *Biochem. J.* 334:819-825 (1999).
NCBI, Accession No. AB103375, dated Aug. 10, 2005.
NCBI, Accession No. AB103376, dated Aug. 10, 2005.
NCBI, Accession No. Q5FVI9, dated May 10, 2005.
English Language International Search Report for PCT/JP2007/058079, mailed Jul. 3, 2007.

* cited by examiner

*Primary Examiner* — Karen Carlson
(74) *Attorney, Agent, or Firm* — Clark & Elbing LLP

(57) ABSTRACT

An object of the invention is to provide a dephosphorylation enzyme that regulates cardiomyocyte differentiation, dominant negative enzyme thereof, a gene encoding the enzyme protein and use thereof. A protein or the like consisting of any one of the following amino acid sequences (A) to (C) is used:
(A) the amino acid sequence of SEQ ID NO:2;
(B) an amino acid sequence wherein one or several amino acids except for cysteine at position 138 are deleted, substituted or added in the amino acid sequence of SEQ ID NO:2, wherein a protein consisting of the amino acid sequence has a dual specificity phosphatase activity; and
(C) an amino acid sequence having at least 60% or more homology to the amino acid sequence of SEQ ID NO:2 and having cysteine at position 138, wherein a protein consisting of the amino acid sequence has a dual specificity phosphatase activity.

1 Claim, 15 Drawing Sheets

SEQUENCE LISTING

```
<160> NUMBER OF SEQ ID NOS: 8

<210> SEQ ID NO 1
<211> LENGTH: 937
<212> TYPE: DNA
<213> ORGANISM: Homo sapiens

<400> SEQUENCE: 1
aattcggcac gagggctcag gcagagtcct gccccctgcac ccactccccc attcccggcc      60
ccaggccatg ccccaggatg gactcactgc agaagcagga cctccggagg cccaagatcc     120
atggggcagt ccaggcatct ccctaccagc cgcccacatt ggcttcgctg cagcgcttgc     180
tgtgggtccg tcaggctgcc acactgaacc atatcgatga ggtctggccc agcctcttcc     240
tgggagatgc gtacgcagcc cgggacaaga gcaagctgat ccagctggga atcacccacg     300
ttgtgaatgc cgctgcaggc aagttccagg tggacacagg tgccaaattc taccgtggaa     360
```

```
tgtccctgga gtactatggc atcgaggcgg acgacaaccc cttcttcgac ctcagtgtct    420
actttctgcc tgttgctcga tacatccgag ctgccctcag tgttccccaa ggccgcgtgc    480
tggtacactg tgccatgggg gtaagccgct ctgccacact tgtcctggcc ttcctcatga    540
tctgtgagaa catgacgctg gtagaggcca tccagacggt gcaggcccac cgcaatatct    600
gccctaactc aggcttcctc cggcagctcc aggttctgga caaccgactg ggcggggaga    660
cggggcggtt ctgatctggc aggcagccag gatccctgac ccttggccca accccaccag    720
cctggccctg ggaacagcag gctctgctgt ttctagtgac cctgagatgt aaacagcaag    780
tgggggctga gcagaggca gggatagctg ggtggtgacc tcttagcggg tggatttccc    840
tgacccaatt cagagattct ttatgcaaaa gtgagttcag tccatctcta aataaaata     900 ttcatcgtca taagaaaaa aaaaaaaaa aaaaaaa                                937

<210> SEQ ID NO 2
<211> LENGTH: 198
<212> TYPE: PRT
<213> ORGANISM: Homo sapiens

<400> SEQUENCE: 2

Met Asp Ser Leu Gln Lys Gln Asp Leu Arg Arg Pro Lys Ile His Gly
1               5                   10                  15

Ala Val Gln Ala Ser Pro Tyr Gln Pro Pro Thr Leu Ala Ser Leu Gln
            20                  25                  30

Arg Leu Leu Trp Val Arg Gln Ala Ala Thr Leu Asn His Ile Asp Glu
        35                  40                  45

Val Trp Pro Ser Leu Phe Leu Gly Asp Ala Tyr Ala Ala Arg Asp Lys
    50                  55                  60

Ser Lys Leu Ile Gln Leu Gly Ile Thr His Val Val Asn Ala Ala Ala
65                  70                  75                  80

Gly Lys Phe Gln Val Asp Thr Gly Ala Lys Phe Tyr Arg Gly Met Ser
                85                  90                  95

Leu Glu Tyr Tyr Gly Ile Glu Ala Asp Asp Asn Pro Phe Phe Asp Leu
            100                 105                 110

Ser Val Tyr Phe Leu Pro Val Ala Arg Tyr Ile Arg Ala Ala Leu Ser
        115                 120                 125

Val Pro Gln Gly Arg Val Leu Val His Cys Ala Met Gly Val Ser Arg
    130                 135                 140

Ser Ala Thr Leu Val Leu Ala Phe Leu Met Ile Cys Glu Asn Met Thr
145                 150                 155                 160

Leu Val Glu Ala Ile Gln Thr Val Gln Ala His Arg Asn Ile Cys Pro
                165                 170                 175

Asn Ser Gly Phe Leu Arg Gln Leu Gln Val Leu Asp Asn Arg Leu Gly
            180                 185                 190

Arg Glu Thr Gly Arg Phe
        195

<210> SEQ ID NO 3
<211> LENGTH: 1665
<212> TYPE: DNA
<213> ORGANISM: Homo sapiens

<400> SEQUENCE: 3
gttggctggg gagcccacgc tgcctggcga ctcgggccac cgaatgtgag accgagtccc     60
tttatgtcac cagcgcacac gctgatttga accctgcttc gacgtgtgtg tcatggctta    120
aaaatagctg ctaatctgtc aacctgtctt gggcagaaac agcggcggcg acagcagcag    180
```

```
gagcgtcatg gccgtggcgc tgtctgcgcc ggcgatccgc ctttcggact gaggcccagc    240
gcagcgcttg caaagagcag cagctacctg caactgaac ccatcatcac cacagccact    300
cctgcagctg ccacggtttc tgccacctct aagatgtgcc ctggtaactg gctttgggct    360
tctatgactt ttatggcccg cttctcccgg agtagctcaa ggtctcctgt tcgaactcga    420
gggaccctgg aggagatgcc aaccgttcaa catcctttcc tcaatgtctt cgagttggag    480
cggctcctct acacaggcaa gacagcctgt aaccatgccg acgaggtctg gccaggcctc    540
tatctcggag accaggacat ggctaacaac cgccgggagc ttcgccgcct gggcatcacg    600
cacgtcctca atgcctcaca cagccggtgg cgaggcacgc ccgaggccta tgaggggctg    660
ggcatccgct acctgggtgt tgaggccac gactcgccag cctttgacat gagcatccac    720
ttccagacgg ctgccgactt catccaccgg gcgctgagcc agccaggagg gaagatcctg    780
gtgcattgtg ctgtgggcgt gagccgatcc gccaccctgg tactggccta cctcatgctg    840
taccaccacc ttaccctcgt ggaggccatc aagaaagtca agaccaccg aggcatcatc    900 cccaaccggg gcttcctgag gcagctcctg gccctggacc gcaggctgcg gcagggtctg    960
gaagcatgag gggagggga gagaggtcag gccaggcccg tgggtaggtc cctggctccc    1020
agctggagat aggaggccca ggtggcaggt agcaggaggc ccagatcacc catcctcccc    1080
tggggtcagg agaggccgag ccccaggcca ctgtcactct ttgtgggagg ggacggggag    1140
tgaggttggg cagtgtggtg gatgggcacc caggaagggt tgaccaggga aggaggcagc    1200
taggctgtag atgaagatg gtcctgggat tcgaacaccg ctgggatctg ccagggtgc    1260 tccctgggat tcacagtccc ttcccctctt tgtgcccaag tgtttccctc tctccctcac    1320
caaaacaaaa gggccatctc tgccctgcac ttgtgcagaa agtcagggat acggcaagca    1380
tgaatgcaat ggtgtagagt tgtgtgaaac ccctagcata gagacagaca gcgaagagat    1440
ggtgtgaaaa gcttgcagaa ccagacagag aaccccacag actttccact ccaagcacag    1500
gaggaggtag ctagcgtgtg agggttggca ctaggcccac ggctgctgct tgggccaaaa    1560
acatacagag gtgcatggct ggcagtcttg aaattgtcac tcgcttactg gatccaagcg    1620
tctcgaggat aaataaagat catgaaaaaa aaaaaaaaaa aaaaa                     1665
```

<210> SEQ ID NO 4
<211> LENGTH: 211
<212> TYPE: PRT
<213> ORGANISM: Homo sapiens

<400> SEQUENCE: 4

```
Met Cys Pro Gly Asn Trp Leu Trp Ala Ser Met Thr Phe Met Ala Arg
1               5                   10                  15

Phe Ser Arg Ser Ser Arg Ser Pro Val Arg Thr Arg Gly Thr Leu
            20                  25                  30

Glu Glu Met Pro Thr Val Gln His Pro Phe Leu Asn Val Phe Glu Leu
        35                  40                  45

Glu Arg Leu Leu Tyr Thr Gly Lys Thr Ala Cys Asn His Ala Asp Glu
    50                  55                  60

Val Trp Pro Gly Leu Tyr Leu Gly Asp Gln Asp Met Ala Asn Asn Arg
65                  70                  75                  80

Arg Glu Leu Arg Arg Leu Gly Ile Thr His Val Leu Asn Ala Ser His
                85                  90                  95

Ser Arg Trp Arg Gly Thr Pro Glu Ala Tyr Glu Gly Leu Gly Ile Arg
            100                 105                 110
```

```
Tyr Leu Gly Val Glu Ala His Asp Ser Pro Ala Phe Asp Met Ser Ile
        115                 120                 125

His Phe Gln Thr Ala Ala Asp Phe Ile His Arg Ala Leu Ser Gln Pro
    130                 135                 140

Gly Gly Lys Ile Leu Val His Cys Ala Val Gly Val Ser Arg Ser Ala
145                 150                 155                 160

Thr Leu Val Leu Ala Tyr Leu Met Leu Tyr His His Leu Thr Leu Val
                165                 170                 175

Glu Ala Ile Lys Lys Val Lys Asp His Arg Gly Ile Ile Pro Asn Arg
                180                 185                 190

Gly Phe Leu Arg Gln Leu Leu Ala Leu Asp Arg Arg Leu Arg Gln Gly
        195                 200                 205

Leu Glu Ala
    210

<210> SEQ ID NO 5
<211> LENGTH: 27
<212> TYPE: DNA
<213> ORGANISM: Artificial Sequence
<220> FEATURE:
<223> OTHER INFORMATION: Oligonucleotide Primer

<400> SEQUENCE: 5
gaggtcgaca tggactcact gcagaag                                       27

<210> SEQ ID NO 6
<211> LENGTH: 33
<212> TYPE: DNA
<213> ORGANISM: Artificial Sequence
<220> FEATURE:
<223> OTHER INFORMATION: Oligonucleotide Primer

<400> SEQUENCE: 6
aatgcggccg ctctagaacc gccccgtctc ccg                                33

<210> SEQ ID NO 7
<211> LENGTH: 27
<212> TYPE: DNA
<213> ORGANISM: Artificial Sequence
<220> FEATURE:
<223> OTHER INFORMATION: Oligonucleotide Primer

<400> SEQUENCE: 7
gaggtcgaca tgtgccctgg taactgg                                       27

<210> SEQ ID NO 8
<211> LENGTH: 33
<212> TYPE: DNA
<213> ORGANISM: Artificial Sequence
<220> FEATURE:
<223> OTHER INFORMATION: Oligonucleotide Primer

<400> SEQUENCE: 8
aatgcggccg cactaggctt ccagaccctg ccg                                33
```

PHOSPHATASES INVOLVED IN THE REGULATION OF CARDIOMYOCYTE DIFFERENTIATION

CROSS-REFERENCE TO RELATED APPLICATIONS

The present application is the U.S. National Stage of International Application No. PCT/JP2007/058079, filed Apr. 12, 2007, which claims the benefit of Japanese Application Serial No. JP 2006-112524, filed Apr. 14, 2006.

TECHNICAL FIELD

The present invention relates to dephosphorylation enzymes that regulate cardiomyocyte differentiation and dominant negative enzymes thereof.

BACKGROUND ART

Phosphorylation signals are conserved in eukaryotes and play an important role in various physiological processes. Among those, abnormal phosphorylation of tyrosine residues is known to play a key role in the onset of many hereditary and acquired diseases. Currently, therefore, many tyrosine kinase inhibitors are clinically applied.

On the other hand, dephosphorylation enzyme termed phosphatases inactivates a phosphorylation signal pathway by dephosphorylating a certain site in the pathway. Among the dephosphorylation enzymes, tyrosine dephosphorylation enzymes have been being elucidated to function specifically and initiatively in the regulation of various physiological processes (see Non-Patent Documents 1-3). For example, 14 tyrosine dephosphorylation enzymes have been so far identified as a responsible gene for an autoimmune disease, diabetes, hereditary disease, and muscular disease. In addition, there are at least 30 known tyrosine dephosphorylation enzymes associated with the onset of cancer (see Non-Patent Document 4). Currently, however, since their physiological roles and target pathways are not elucidated, development of clinically applicable tyrosine dephosphorylation enzyme inhibitors has not been advanced well yet (see Non-Patent Document 5).

The present inventors have identified or cloned two dual specificity phosphatases (DSPs), which are a kind of tyrosine dephosphorylation enzyme, from human cells by using degenerate polymerase chain reaction (PCR) and expression sequence tag (EST) data search (GenBank accession No. AB103375; GenBank accession No. AB103376). These DSPs are now known as DUSP13 and DUSP26, respectively. For DUSP13, mouse homologue TMDP (testis- and skeletal muscle-specific DSP) is known. TMDP expression is specific to testis and skeletal muscle in mouse. Mouse TMDP is pointed out to be involved in spermatogenesis (see Non-Patent Document 6).

However, it remains to be known about physiological roles of human DUSP13 and DUSP26. Furthermore, there has been no report on a tyrosine dephosphorylation enzyme with regard to its physiological roles in heart and its relation to heart diseases.

[Non-Patent Document 1] Hunter T (1989) Cell. 58: 1013-1016
[Non-Patent Document 2] Mustelin T (2002) Curr Dir Autoimmun. 5: 176-190
[Non-Patent Document 3] Mustelin T et. al. (2002) Front Biosci. 7: 918-969
[Non-Patent Document 4] Andersen J N et. al. (2004) FASEB J. 18: 8-30
[Non-Patent Document 5] Alonso A et. al. (2004) Cell. 117: 699-711
[Non-Patent Document 6] Biochem. J. (1999) 344: 819-825

DISCLOSURE OF THE INVENTION

Object to be Solved by the Invention

An object of the present invention is to provide dephosphorylation enzymes that regulates cardiomyocyte differentiation and their dominant negative enzymes thereof. It is also an object of the present invention to provide a DNA encoding such an enzyme protein and a method for using the same.

Means to Solve the Object

The present inventors have found out that the amino acid sequence of SEQ ID NO:2 and the amino acid sequence of SEQ ID NO:4 are dual specificity phosphatases involved in the regulation of cardiomyocyte differentiation, thereby completing the present invention. Furthermore, the present inventors have found out that substitution of cysteine at position 138 in the amino acid sequence of SEQ ID NO:2 with another amino acid leads to loss of the dual specificity phosphatase activity and that substitution of cysteine at position 152 in the amino acid sequence of SEQ ID NO:4 with another amino acid leads to loss of the dual specificity phosphatase activity, thereby completing the present invention.

Namely, the present invention relates to (1) a DNA consisting of any one of the following nucleotide sequences (A) to (F):
(A) a nucleotide sequence encoding a protein consisting of the amino acid sequence of SEQ ID NO:2;
(B) a nucleotide sequence encoding a protein consisting of an amino acid sequence wherein one or several amino acids except for cysteine at position 138 are deleted, substituted or added in the amino acid sequence of SEQ ID NO:2, wherein the protein has a dual specificity phosphatase activity;
(C) a nucleotide sequence encoding a protein consisting of an amino acid sequence having at least 60% or more homology to the amino acid sequence of SEQ ID NO:2 and having cysteine at position 138, wherein the protein has dual specificity phosphatase activity;
(D) a nucleotide sequence consisting of the nucleotide position 78 to 674 of SEQ ID NO:1;
(E) a nucleotide sequence consisting of the nucleotide position 78 to 674 of SEQ ID NO:1 wherein one or several nucleotides are deleted, substituted or added, which encodes a protein having cysteine at position 138 and having a dual specificity phosphatase activity; and
(F) a nucleotide sequence hybridizing to a nucleotide sequence consisting of the nucleotide position 78 to 674 of SEQ ID NO:1 under stringent conditions, which encodes a protein having cysteine at position 138 and having a dual specificity phosphatase activity;
(2) a protein consisting of any one of the following amino acid sequences (A) to (C):
(A) the amino acid sequence of SEQ ID NO:2;
(B) an amino acid sequence wherein one or several amino acids except for cysteine at position 138 are deleted, substituted or added in the amino acid sequence of SEQ ID NO:2, wherein a protein consisting of the amino acid sequence has a dual specificity phosphatase activity; and
(C) an amino acid sequence having at least 60% or more homology to the amino acid sequence of SEQ ID NO:2 and having cysteine at position 138, wherein a protein consisting of the amino acid sequence has a dual specificity phosphatase activity;
(3) a DNA consisting of any one of the following nucleotide sequences (A) to (F):
(A) a nucleotide sequence encoding a protein consisting of the amino acid sequence of SEQ ID NO:4;
(B) a nucleotide sequence encoding a protein consisting of an amino acid sequence wherein one or several amino acids except for cysteine at position 152 are deleted, substituted or added in the amino acid sequence of SEQ ID NO:4, wherein the protein has a dual specificity phosphatase activity;
(C) a nucleotide sequence encoding a protein consisting of an amino acid sequence having at least 60% or more homology to the amino acid sequence of SEQ ID NO:4 and having cysteine at position 152, wherein the protein has a dual specificity phosphatase activity;
(D) a nucleotide sequence consisting of the nucleotide position 334 to 969 of SEQ ID NO:3;
(E) a nucleotide sequence consisting of the nucleotide position 334 to 969 of SEQ ID NO:3, wherein one or several nucleotides are deleted, substituted or added, which encodes a protein having cysteine at position 152 and having a dual specificity phosphatase activity;
(F) a nucleotide sequence hybridizing to a nucleotide sequence consisting of the nucleotide position 334 to 969 of SEQ ID NO:3 under stringent conditions, which encodes a protein having cysteine at position 152 and having a dual specificity phosphatase activity;
(4) a protein consisting of any one of the following amino acid sequences (A) to (C):
(A) the amino acid sequence of SEQ ID NO:4;
(B) an amino acid sequence wherein one or several amino acids except for cysteine at position 152 are deleted, substituted or added in the amino acid sequence of SEQ ID NO:4, wherein a protein consisting of the amino acid sequence has a dual specificity phosphatase activity;
(C) an amino acid sequence having at least 60% or more homology to the amino acid sequence of SEQ ID NO:4 and having cysteine at position 152, wherein a protein consisting of the amino acid sequence has a dual specificity phosphatase activity;
(5) a protein consisting of any one of the following amino acid sequences (a) to (c):
(a) an amino acid sequence wherein cysteine at position 138 is substituted with another amino acid in the amino acid sequence of SEQ ID NO:2;
(b) an amino acid sequence wherein cysteine at position 138 is substituted with another amino acid and one or several amino acids other than cysteine at position 138 are deleted, substituted or added in the amino acid sequence of SEQ ID NO:2, wherein a protein consisting of the amino acid sequence has an inhibitory activity against a dual specificity phosphatase;
(c) an amino acid sequence having at least 60% or more homology to the amino acid sequence of SEQ ID NO: 2 and having at position 138 an amino acid other than cysteine, wherein a protein consisting of the amino acid sequence has an inhibitory activity against a dual specificity phosphatase;
(6) a protein consisting of any one of the following amino acid sequences (a) to (c):
(a) an amino acid sequence wherein cysteine at position 152 is substituted with another amino acid in the amino acid sequence of SEQ ID NO:4;
(b) an amino acid sequence wherein cysteine at position 152 is substituted with another amino acid and one or several amino acids other than cysteine at position 152 are deleted, substituted or added in the amino acid sequence of SEQ ID NO:4, wherein a protein consisting of the amino acid sequence has an inhibitory activity against a dual specificity phosphatase;
(c) an amino acid sequence having at least 60% or more homology to the amino acid sequence of SEQ ID NO: 4 and having at position 152 an amino acid other than cysteine, wherein a protein consisting of the amino acid sequence has an inhibitory activity against a dual specificity phosphatase;
(7) a DNA consisting of a nucleotide sequence encoding the protein recited in the above (5); (8) a DNA consisting of a nucleotide sequence encoding the protein recited in the above (6); (9) the protein recited in the above (4) or (5), wherein the protein has an activity to promote cardiomyocyte differentiation; and (10) the protein recited in the above (2) or (6), wherein the protein has an activity to suppress cardiomyocyte differentiation.

The present invention further relates to (11) a fusion protein wherein the protein recited in the above (4) or (5) is linked with a marker protein and/or a peptide tag; and (12) a fusion protein wherein the protein recited in the above (2) or (6) is linked with a marker protein and/or a peptide tag.

The present invention further relates to (13) a recombinant vector comprising the DNA recited in the above (1) and capable of expressing a protein having a dual specificity phosphatase activity; (14) a recombinant vector comprising the DNA recited in the above (3) and capable of expressing a protein having a dual specificity phosphatase activity; (15) a recombinant vector comprising the DNA recited in the above (7) and capable of expressing a protein having an inhibitory activity against dual specificity phosphatase; and (16) a recombinant vector comprising the DNA recited in the above (8) and capable of expressing a protein having an inhibitory activity against dual specificity phosphatase.

The present invention further relates to (17) a transformant into which the recombinant vector recited in the above (13) or (14) is introduced, which expresses a protein having a dual specificity phosphatase activity; and (18) a transformant into which the recombinant vector recited in the above (15) or (16) is introduced, which expresses a protein having an inhibitory activity against dual specificity phosphatase.

The present invention further relates to (19) a promoting agent for cardiomyocyte differentiation, which comprises the protein recited in the above (4) or (5), the fusion protein recited in the above (11), or the recombinant vector recited in the above (14) or (15); and (20) an inhibitory agent for cardiomyocyte differentiation, which comprises the protein recited in the above (2) or (6), the fusion protein recited in the above (12), or the recombinant vector recited in the above (13) or (16).

The present invention further relates to (21) a method of screening for a substance that promotes or suppresses cardiomyocyte differentiation, comprising the step of culturing in the presence of a test substance a transformed cardiomyocyte into which the recombinant vector recited in the above (13) is introduced, which is capable of expressing the protein recited in the above (2), and measuring and evaluating the degree of cardiomyocyte differentiation; (22) a method of screening for a substance that promotes or suppresses cardiomyocyte differentiation, comprising the step of culturing in the presence of a test substance a transformed cardiomyocyte into which the recombinant vector recited in the above (14) is introduced, which is capable of expressing the protein recited in the above (4), and measuring and evaluating the degree of cardiomyocyte differentiation; (23) a method of screening for a substance that promotes or suppresses cardiomyocyte differentiation, comprising the steps of culturing in the presence of a test substance a transformed cardiomyocyte into which the recombinant vector recited in the above (15) is introduced, which is capable of expressing the protein recited in the above (5), and measuring and evaluating the degree of cardiomyocyte differentiation; and (24) a method of screening for a substance that promotes or suppresses cardiomyocyte differentiation, comprising the step of culturing in the presence of a test substance a transformed cardiomyocyte into which the recombinant vector recited in the above (16) is introduced, which is capable of expressing the protein recited in the above (6), and measuring and evaluating the degree of cardiomyocyte differentiation.

The present invention further relates to (25) use of the DNA recited in the above (1) or (3) for preparing a protein having a dual specificity phosphatase activity; and (26) use of the DNA recited in the above (5) or (6) for preparing a protein having an inhibitory activity against dual specificity phosphatase.

The present invention further relates to (27) a method for activating promotion of cardiomyocyte differentiation using the protein recited in the above (4) or (5); and (28) a method for activating suppression of cardiomyocyte differentiation using the protein recited in the above (2) or (6).

The present invention further relates to (29) a method for preparing a dephosphorylated amino acid from a phosphorylated amino acid using the protein recited in the above (2) or (4).

Further, the present invention relates to (30) an antibody that specifically binds to the protein recited in any one of the above (2), (4), (5) or (6).

BRIEF DESCRIPTION OF DRAWINGS

FIG. 1 shows the amino acid sequences of human DUSP13 and human DUSP26, and the nucleotide sequences encoding them. In the figure, gray boxes represent catalytic domains of the dephosphorylation enzymes. In addition, double underlined regions represent sequences of each peptide used to immunize a rabbit for the production of antibodies.

FIG. 2 shows an alignment of human DUSP13 and mouse DUSP13 (FIG. 2, left) and an alignment of human DUSP26 and mouse DUSP26 (FIG. 2, right). In the figure, gray boxes represent catalytic domains of the dephosphorylation enzymes. In addition, double underlined regions represent sequences of each peptide used to immunize a rabbit for the production of antibodies.

FIG. 5 shows the subcellular localization (left) and the subcellular fractionation (right) of human DUSP13 protein, human DUSP26 and the like.

BEST MODE FOR CARRYING OUT THE INVENTION

Figure 3:
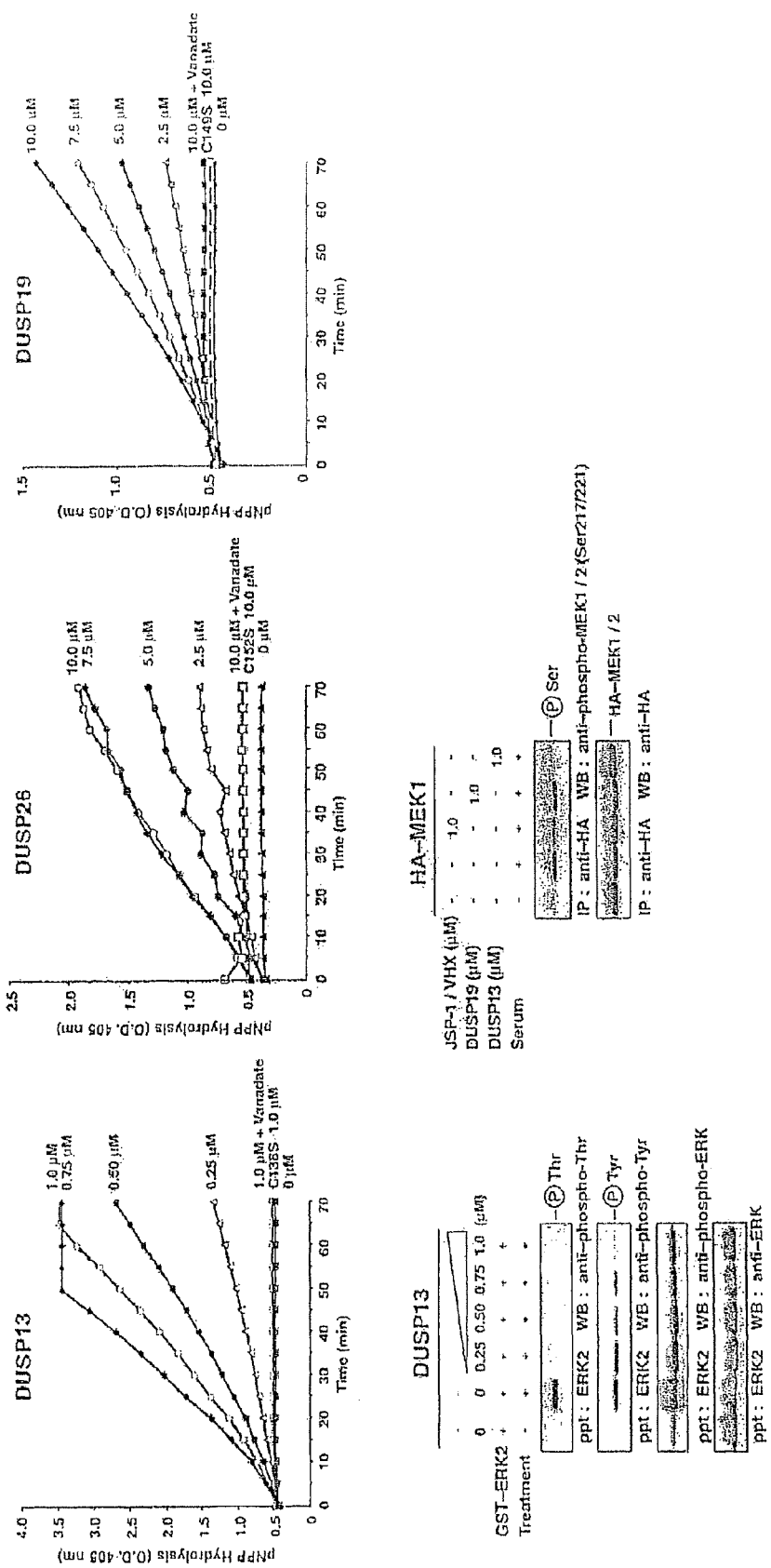
FIG. 3 shows the results of the test for in vitro dephosphorylation activity of human DUSP13, human DUSP26, and their CS mutants.

A DNA of the present invention is not particularly limited as long as the DNA consists of any one of the following nucleotide sequences: (1)-(A) a nucleotide sequence encoding the amino acid sequence of SEQ ID NO:2; (3)-(A) a nucleotide sequence encoding the amino acid sequence of SEQ ID NO:4; (1)-(B) a nucleotide sequence encoding a protein consisting of an amino acid sequence wherein one or several amino acids except for cysteine at position 138 are deleted, substituted or added in the amino acid sequence of SEQ ID NO:2, wherein the protein has a dual specificity phosphatase activity; (3)-(B) a nucleotide sequence encoding a protein consisting of an amino acid sequence wherein one or several amino acids except for cysteine at position 152 are deleted, substituted or added in the amino acid sequence of SEQ ID NO:4, wherein the protein has a dual specificity phosphatase activity; (1)-(C) a nucleotide sequence encoding a protein consisting of an amino acid sequence having at least 60% or more homology to the amino acid sequence of SEQ ID NO:2 and having cysteine at position 138, wherein the protein has a dual specificity phosphatase activity; (3)-(C) a nucleotide sequence encoding a protein consisting of an amino acid sequence having at least 60% or more homology to the amino acid sequence of SEQ ID NO:4 and having cysteine at position 152, wherein the protein has a dual specificity phosphatase activity; (1)-(D) a nucleotide sequence consisting of the nucleotide position 78 to 674 of SEQ ID NO:1; (3)-(D) a nucleotide sequence consisting of the nucleotide position 334 to 969 of SEQ ID NO:3; (1)-(E) a nucleotide sequence consisting of the nucleotide position 78 to 674 of SEQ ID NO:1 wherein one or several nucleotides are deleted, substituted or added, which encodes a protein having cysteine at position 138 and having a dual specificity phosphatase activity; (3)-(E) a nucleotide sequence consisting of the nucleotide position 334 to 969 of SEQ ID NO:3 wherein one or several nucleotides are deleted, substituted or added, which encodes a protein having cysteine at position 152 and having a dual specificity phosphatase activity; (1)-(F) a nucleotide sequence hybridizing to a nucleotide sequence consisting of the nucleotide position 78 to 674 of SEQ ID NO:1 under stringent conditions, which encodes a protein having cysteine at position 138 and having a dual specificity phosphatase activity; (3)-(F) a nucleotide sequence hybridizing to a nucleotide sequence consisting of the nucleotide position 334 to 969 of SEQ ID NO:3 under stringent conditions, which encodes a protein having cysteine at position 152 and having a dual specificity phosphatase activity; and a nucleotide sequence encoding a protein consisting of any one of the amino acid sequences (a) to (c) mentioned below.

Further, a protein of the present invention is not particularly limited as long as it is a protein consisting of any one of the following amino acid sequences: (2)-(A) the amino acid sequence of SEQ ID NO:2; (4)-(A) the amino acid sequence of SEQ ID NO:4; (2)-(B) an amino acid sequence wherein one or several amino acids except for cysteine at position 138 are deleted, substituted or added in the amino acid sequence of SEQ ID NO: 2, wherein a protein consisting of the amino acid sequence has a dual specificity phosphatase activity; (4)-(B) an amino acid sequence wherein one or several amino acids except for cysteine at position 152 are deleted, substituted or added in the amino acid sequence of SEQ ID NO:4, wherein a protein consisting of the amino acid sequence has a dual specificity phosphatase activity; (2)-(C) an amino acid sequence having at least 60% or more homology to the amino acid sequence of SEQ ID NO:2 and having cysteine at position 138, wherein a protein consisting of the amino acid sequence has a dual specificity phosphatase activity; (4)-(C) an amino acid sequence having at least 60% or more homology to the amino acid sequence of SEQ ID NO:4 and having cysteine at position 152, wherein a protein consisting of the amino acid sequence has a dual specificity phosphatase activity; (5)-(a) an amino acid sequence wherein cysteine at position 138 is substituted with another amino acid in the amino acid sequence of SEQ ID NO:2; (6)-(a) an amino acid sequence wherein cysteine at position 152 is substituted with another amino acid in the amino acid sequence of SEQ ID NO:4; (5)-(b) an amino acid sequence wherein cysteine at position 138 is substituted with another amino acid and one or several amino acids other than cysteine at position 138 are deleted, substituted or added in the amino acid sequence of SEQ ID NO:2, wherein a protein consisting of the amino acid sequence has an inhibitory activity against a dual specificity phosphatase; (6)-(b) an amino acid sequence wherein cysteine at position 152 is substituted with another amino acid and one or several amino acids other than cysteine at position 152 are deleted, substituted or added in the amino acid sequence of SEQ ID NO:4, and wherein a protein consisting of the amino acid sequence has an inhibitory activity against a dual specificity phosphatase; (5)-(c) an amino acid sequence having at least 60% or more homology to the amino acid sequence of SEQ ID NO:2 and having at position 138 an amino acid other than cysteine, wherein a protein consisting of the amino acid sequence has an inhibitory activity against a dual specificity phosphatase; (6)-(c) an amino acid sequence having at least 60% or more homology to the amino acid sequence of SEQ ID NO:4 and having at position 152 an amino acid other than cysteine, wherein a protein consisting of the amino acid sequence has an inhibitory activity against a dual specificity phosphatase.

As used herein, a "protein having a dual specificity phosphatase activity" means a tyrosine phosphatase, which can dephosphorylate a phosphorylated tyrosine, further having an activity to dephosphorylate a phosphorylated serine or threonine. Whether a protein has the dual specificity phosphatase activity or not can be easily confirmed by examining whether or not phosphorylated serines or threonines in addition to phosphorylated tyrosines are dephosphorylated when the protein is acted on an appropriate phosphorylated substrate such as phosphorylated ERK or phosphorylated MEK in an appropriate solvent.

As used herein, a "protein having an inhibitory activity against a dual specificity phosphatase" means, for example, when a protein having an inhibitory activity against a dual specificity phosphatase (hereinafter referred to as "protein A") and a protein having a dual specificity phosphatase activity of the present invention (hereinafter referred to as "protein B") coexist in the same mole concentration, the dephosphorylation activity of the protein B becomes 90% or less, preferably 70% or less, more preferably 50% or less and even preferably 30% or less as compared to that when the protein A does not coexist. A substrate used in the measurement of dephosphorylation activity may be any one of known substances, and ERK2 can be exemplified.

Further, among the proteins of the present invention, (A) a protein consisting of the amino acid sequence of SEQ ID NO:4 and (a) a protein consisting of an amino acid sequence wherein cysteine at position 138 is substituted with another amino acid in the amino acid sequence of SEQ ID NO:2 have an activity to regulate animal cardiomyocyte differentiation, particularly an activity to promote rat cardiomyocyte differentiation. Among the proteins of the present invention, a protein consisting of (B) an amino acid sequence wherein one or several amino acids except for cysteine at position 152 are deleted, substituted or added in the amino acid sequence of SEQ ID NO:4, wherein a protein consisting of the amino acid sequence has a dual specificity phosphatase activity, (C) an amino acid sequence having at least 60% or more homology to the amino acid sequence of SEQ ID NO:4 and having cysteine at position 152, wherein a protein consisting of the amino acid sequence has a dual specificity phosphatase activity, (b) an amino acid sequence wherein cysteine at position 138 is substituted and one or several amino acids other than cysteine at position 138 are deleted, substituted or added in the amino acid sequence of SEQ ID NO:2, wherein a protein consisting of the amino acid sequence has an inhibitory activity against dual specificity phosphatase, or (c) an amino acid sequence having at least 60% or more homology to the amino acid sequence of SEQ ID NO:2 and having at position 138 an amino acid other than cysteine, wherein a protein consisting of the amino acid sequence has an inhibitory activity against dual specificity phosphatase may not have an activity to regulate animal cardiomyocyte differentiation, but preferably have an activity to regulate animal cardiomyocyte differentiation, particularly rat cardiomyocyte differentiation. In the present invention, an activity to regulate animal cardiomyocyte differentiation refers to an activity to promote or suppress animal cardiomyocyte differentiation. Although the animal in this context is not particularly limited as long as it is an animal, the animal is preferably mammal, more preferably human, rat, mouse or rabbit and even more preferably human, rat or mouse.

Further, among the proteins of the present invention, (A) a protein consisting of the amino acid sequence of SEQ ID NO:2 has an activity to regulate animal cardiomyocyte differentiation, particularly an activity to suppress rat cardiomyocyte differentiation. Further, (a) a protein consisting of an amino acid sequence wherein cysteine at position 152 is substituted with another amino acid in the amino acid sequence of SEQ ID NO:4 may have the same effect.

Among the proteins of the present invention, a protein consisting of (B) an amino acid sequence wherein one or several amino acids except for cysteine at position 138 are deleted, substituted or added in the amino acid sequence of SEQ ID NO:2, wherein a protein consisting of the amino acid sequence has a dual specificity phosphatase activity, (C) an amino acid sequence having at least 60% or more homology to the amino acid sequence of SEQ ID NO:2 and having cysteine at position 138, wherein a protein consisting of the amino acid sequence has a dual specificity phosphatase activity, (b) an amino acid sequence wherein cysteine at position 152 is substituted with another amino acid and one or several amino acids other than cysteine at position 152 are deleted, substituted or added in the amino acid sequence of SEQ ID NO:4, wherein a protein consisting of the amino acid sequence has an inhibitory activity against dual specificity phosphatase, or (c) an amino acid sequence having at least 60% or more homology to the amino acid sequence of SEQ ID NO: 4 and having at position 152 an amino acid other than cysteine, wherein a protein consisting of the amino acid sequence has an inhibitory activity against dual specificity phosphatase, may not have an activity to regulate animal cardiomyocyte differentiation, but preferably has an activity to regulate animal cardiomyocyte differentiation, particularly an activity to suppress rat cardiomyocyte differentiation.

A protein can be easily confirmed for its activity to promote animal cardiomyocyte differentiation or activity to suppress animal cardiomyocyte differentiation by, for example, comparing the degree of cardiomyocyte differentiation between the cases where rat cardiomyocyte H9c2 is cultured with said protein expressed and where H9c2 is cultured without said protein expressed. The degree of differentiation can be determined by examining the expression level of any one or more proteins of MyHC (Myosin Heavy Chain), Myogenin, and Troponin T. All of these proteins MyHC (Myosin Heavy Chain), Myogenin, and Troponin T tend to increase in the expression levels as differentiation proceeds. For other animals, besides rat, an activity to promote or suppress cardiomyocyte differentiation can be easily confirmed by a similar method.

Examples of a DNA consisting of the above-described nucleotide sequence consisting of the nucleotide position 78 to 674 of SEQ ID NO:1 include human DUSP13 (hDUSP13) gene. Examples of a protein consisting of the amino acid sequence of SEQ ID NO:2 include human DUSP13 protein. Examples of a DNA consisting of the above-described nucleotide sequence consisting of the nucleotide position 334 to 969 of SEQ ID NO:3 include human DUSP26 (hDUSP26) gene. Examples of a protein consisting of the amino acid sequence of SEQ ID NO:4 include human DUSP26 protein.

As used herein, "an amino acid sequence wherein one or several amino acids are deleted, substituted or added" means an amino acid sequence in which, for example, any number of 1 to 20, preferably 1 to 15, more preferably 1 to 10, even more preferably 1 to 5 amino acids are deleted, substituted or added. Further, "a nucleotide sequence wherein one or several nucleotides are deleted, substituted or added" as used herein means a nucleotide sequence in which, for example, any numbers of 1 to 20, preferably 1 to 15, more preferably 1 to 10, even more preferably 1 to 5 nucleotides are deleted, substituted or added.

For example, a DNA consisting of a nucleotide sequence wherein one or several nucleotides are deleted, substituted or added (mutant DNA) may be produced by any method known to those skilled in the art such as chemical synthesis, genetic engineering technique or mutagenesis. Specifically, a mutant DNA may be obtained by introducing a mutation into a DNA consisting of the nucleotide sequence of SEQ ID NO:1 or 3 by using, for example, a method of bringing a mutagenic agent into contact with the DNA, a method of irradiating the DNA with ultraviolet rays, or a genetic engineering technique. Site-directed mutagenesis is one of genetic engineering techniques, which is useful because it enables introduction of a specific mutation into a specific site. Such a technique can be performed according to a method described in, for example, Molecular Cloning: A laboratory Manual, 2nd Ed., Cold Spring Harbor Laboratory, Cold Spring Harbor, N.Y., 1989. (hereinafter referred to as "Molecular Cloning, 2nd ed." for short) or Current Protocols in Molecular Biology, Supplement 1-38, John Wiley & Sons (1987-1997). A protein consisting of an amino acid sequence wherein one or several amino acids are deleted, substituted or added can be obtained by expressing the mutant DNA by using an appropriate expression system. In addition, by using a similar method, a DNA consisting of a nucleotide sequence encoding an amino acid sequence wherein cysteine at position 138 is substituted with another amino acid in the amino acid sequence of SEQ ID NO:2, and a DNA consisting of a nucleotide sequence encoding an amino acid sequence wherein cysteine at position 152 is substituted with another amino acid in the amino acid sequence of SEQ ID NO:4 can be obtained. Furthermore, by expressing such a DNA with an appropriate expression system, a protein consisting of an amino acid sequence wherein cysteine at position 138 is substituted with another amino acid in the amino acid sequence of SEQ ID NO:2 can be obtained.

A "nucleotide sequence hybridizing under stringent conditions" as used herein means a nucleotide sequence obtained by a method such as colony hybridization, plaque hybridization or southern blot hybridization using a nucleic acid such as DNA or RNA as a probe. Specifically exemplified is a DNA that can be identified by carrying out hybridization at 65° C. in the presence of 0.7 to 1.0 M NaCl using a filter to which a colony- or plaque-derived DNAs or fragments thereof are fixed, followed by washing the filter using about 0.1 to 2×SSC solution (1×SSC: 150 mM sodium chloride, 15 mM sodium citrate) at 65° C. Hybridization can be carried out according to a method described in Molecular Cloning, 2nd ed.

Examples of a DNA hybridizing under stringent conditions include a DNA having a homology of above a certain level to a nucleotide sequence of a DNA used as a probe. Preferred examples include a DNA having a homology of 60% or more, preferably 70% or more, more preferably 80% or more, even more preferably 90% or more, particularly preferably 95% or more, and most preferably 98% or more to a nucleotide sequence of a DNA used as a probe.

A method to obtain or prepare a DNA of the present invention is not particularly limited and the DNA of interest can be isolated by preparing an appropriate probe or primer based on the nucleotide sequence information shown in SEQ ID NO:1 or 3 or the amino acid sequence information shown in SEQ ID NO:2 or 4 described herein and screening a cDNA library expected to contain the DNA with the probe or primer. Alternatively, the DNA of interest may be prepared by chemical synthesis according to a conventional method.

Specifically, a DNA of the present invention can be obtained by generating a cDNA library according to a conventional method from human, from which DNAs of the present invention were isolated, and selecting a desired clone from the library by using an appropriate probe specific to a DNA of the present invention. Examples of a source for the above-described cDNA include various cells and tissues derived from human. Further, isolation of total RNA, isolation and purification of mRNA, and acquisition and cloning of cDNA from these cells and tissues can be performed according to a conventional method. Examples of a method to screen cDNA library for a DNA of the present invention include a conventional method commonly used by those skilled in the art, such as a method described in Molecular Cloning, 2nd ed.

Further, a mutant DNA or homologous DNA of the present invention consisting of any one of the above-described nucleotide sequences (A) to (C) and (E) to (F) can be isolated by carrying out a screening of the DNA homologue from other organisms or the like under appropriate conditions by using a DNA fragment comprising a nucleotide sequence consisting of the nucleotide position 78 to 674 of SEQ ID NO:1 or comprising a part thereof. Alternatively, it can be prepared by the above-described method for producing a mutant DNA.

A method to obtain or prepare a protein of the present invention is not particularly limited and the protein may be any of a naturally occurring protein, chemically synthesized protein, or a recombinant protein produced by genetic engineering. A protein of the present invention as a naturally occurring protein can be obtained by appropriately combining methods of isolation and purification of the protein from a cell or tissue expressing the protein. When a protein is prepared by chemical synthesis, a protein of the present invention can be synthesized according to a chemical synthesis method such as Fmoc method (fluorenylmethyloxycarbonyl method) or tBoc method (t-butyloxycarbonyl method). Further, a protein of the present invention can be synthesized by using various commercially available peptide synthesizers. When a protein is prepared by genetic engineering, a protein of the present invention can be prepared by introducing a DNA consisting of a nucleotide sequence encoding the protein into a suitable expression system. Among these, preferred is the preparation by genetic engineering, which is relatively easy to operate and enables large-scale preparation.

For example, when a protein of the present invention is prepared using a genetic engineering technique, a known method is available to recover and purify the protein from the cell culture. Such method includes ammonium sulfate precipitation or ethanol precipitation, acid extraction, anion- or cation-exchange chromatography, phosphocellulose chromatography, hydrophobic interaction chromatography, affinity chromatography, hydroxyapatite chromatography, and lectin chromatography. Preferably, high-performance liquid chromatography is used. In particular, purified protein can be obtained by using an affinity chromatography column on which an antibody such as a monoclonal antibody against a protein of the present invention is immobilized. Alternatively, when a generally used peptide tag is added to the above protein of the present invention, an affinity chromatography column on which substance having affinity for the peptide tag is immobilized can be used. Further, when a protein of the present invention is expressed in cell membrane, purified preparation can be obtained by treating the cell membrane with a cell membrane-degrading enzyme and then carrying out the above-described purification procedure.

Furthermore, those skilled in the art could appropriately prepare or obtain a protein consisting of an amino acid sequence wherein one or several amino acids are deleted, substituted or added in the amino acid sequence of SEQ ID NO:2 or 4, or a protein consisting of an amino acid sequence having at least 60% or more homology to the amino acid sequence of SEQ ID NO:2 or 4, based on the nucleotide sequence information shown in SEQ ID NO:1 or 3 which shows an example of nucleotide sequences encoding the amino acid sequence of SEQ ID NO:2 or 4. For example, a homologue of the DNA can be isolated from an organism other than human by carrying out screening under appropriate conditions using, as a probe, a DNA having a nucleotide sequence of SEQ ID NO:1 or 3 or a part thereof. The protein encoded by the homologous DNA can be prepared by cloning the full-length DNA of the homologous DNA, then introducing the DNA into an expression vector, and expressing the DNA in an appropriate host.

A fusion protein of the present invention is not limited as long as it is a fusion protein wherein the proteins of the present invention are linked with a marker protein and/or a peptide tag. A marker protein is not particularly limited as long as it is a conventionally known marker protein. Specific examples include enzymes such as alkaline phosphatases and HRP (Horse Radish Peroxidase), Fc regions of antibodies, and fluorescent substances such as GFP (Green Fluorescent Protein). Specific examples of a peptide tag in the present invention include conventionally known peptide tags such as epitope tags (e.g., HA (hemagglutinin), FLAG, and Myc) and affinity tags (e.g., GST (glutathione S-transferase), maltose-binding proteins, biotinylated peptide, and oligohistidine). Such fusion peptides can be generated by a conventional method and are useful for purification of a protein of the present invention, detection of a protein of the present invention, quantification of an antibody against a protein of the present invention, or other research reagents in the art utilizing the affinity between glutathione Sepharose and GST tag.

A recombinant vector of the present invention is not particularly limited as long as it contains said DNA of the present invention and is capable of expressing a protein having a dual specificity phosphatase activity. A recombinant vector of the present invention can be constructed by appropriately integrating a DNA of the present invention into an expression vector. As such an expression vector, preferred are those self-replicable in a host cell and those capable of being integrated into a chromosome of a host cell. Further, an expression vector containing a regulatory sequence such as promoter, enhancer or terminator at a position where a DNA of the present invention can be expressed can be suitably used.

Examples of an expression vector for animal cells include pEGFP-C1 (Clontech Laboratories Inc.), pGBT-9 (Clontech Laboratories Inc.), pcDNAI (INVITROGEN), pcDNA3.1 (INVITROGEN), pEF-BOS (Nucleic Acids Res., 18, 5322, 1990), pAGE107 (Cytotechnology, 3, 133, 1990), pCDM8 (Nature, 329, 840, 1987), pcDNAI/AmP (INVITROGEN), pREP4 (INVITROGEN), pAGE103 (J. Biochem., 101, 1307, 1987), and pAGE210. Examples of a promoter for animal cells include cytomegalovirus (human CMV) IE (immediate early) gene promoter, SV40 early promoter, retrovirus promoter, metallothionein promoter, heat shock promoter, and SRα promoter.

Examples of an expression vector for yeast include pYES2 (INVITROGEN), YEp13 (ATCC37115), YEp24 (ATCC37051), Ycp50 (ATCC37419), pHS19 and pHS15. Specific examples of a promoter for yeast include promoters such as PHO5 promoter, PGK promoter, GAP promoter, ADH promoter, gal1 promoter, gal10 promoter, heat shock protein promoter, MFα1 promoter and CUP1 promoter. As an expression vector, although those for animal cells, those for yeast, or the like can be used, preferred is a recombinant vector employing an expression vector for animal cells.

Further, a transformant of the present invention is not particularly limited as long as it is a transformant into which the above-mentioned recombinant vector of the present invention is introduced, which transformant expresses a protein having a dual specificity phosphatase activity. Examples of a transformant include a transformed animal (cell, tissue, body) and a transformed yeast. Among these, a transformed animal (cell, tissue, body) is preferred.

Examples of a host yeast used for generating a transformed yeast include *Saccharomyces cerevisae, Schizosaccharomyces pombe, Kluyveromyces lactis, Trichosporon pullulans*, and *Schwanniomyces alluvius*. Examples of a method for introducing a recombinant vector into a yeast host include electroporation method, spheroplast method, and lithium acetate method.

A promoting agent for cardiomyocyte differentiation of the present invention is not particularly limited as long as it contains any one of the following proteins (I), following fusion proteins (II), or following recombinant vectors of (III) or (IV).

(I) a protein consisting of any one of the following amino acid sequences:
(A) the amino acid sequence of SEQ ID NO:4;
(B) an amino acid sequence wherein one or several amino acids except for cysteine at position 152 are deleted, substituted or added in the amino acid sequence of SEQ ID NO:4, wherein a protein consisting of the amino acid sequence has a dual specificity phosphatase activity;
(C) an amino acid sequence having at least 60% or more homology to the amino acid sequence of SEQ ID NO:4 and having cysteine at position 152, wherein a protein consisting of the amino acid sequence has a dual specificity phosphatase activity;
(a) an amino acid sequence wherein cysteine at position 138 is substituted with another amino acid in the amino acid sequence of SEQ ID NO:2;
(b) an amino acid sequence wherein cysteine at position 138 is substituted with another amino acid and one or several amino acids other than cysteine at position 138 are deleted, substituted or added in the amino acid sequence of SEQ ID NO:2, wherein a protein consisting of the amino acid sequence has an inhibitory activity against a dual specificity phosphatase; and
(c) an amino acid sequence having at least 60% or more homology to the amino acid sequence of SEQ ID NO: 2 and having at position 138 an amino acid other than cysteine, wherein a protein consisting of the amino acid sequence has an inhibitory activity against a dual specificity phosphatase;
(II) a fusion protein wherein any one of the proteins of the above (I) is linked with a marker protein and/or a peptide tag;
(III) a recombinant vector comprising a DNA consisting of any one of the nucleotide sequences below and capable of expressing a protein having a dual specificity phosphatase activity:
(A) a nucleotide sequence encoding a protein consisting of the amino acid sequence of SEQ ID NO:4;
(B) a nucleotide sequence encoding a protein consisting of an amino acid sequence wherein one or several amino acids except for cysteine at position 152 are deleted, substituted or added in the amino acid sequence of SEQ ID NO:4, wherein the protein has a dual specificity phosphatase activity;
(C) a nucleotide sequence encoding a protein consisting of an amino acid sequence having at least 60% or more homology to the amino acid sequence of SEQ ID NO:4 and having cysteine at position 152, wherein the protein has a dual specificity phosphatase activity;
(D) a nucleotide sequence consisting of the nucleotide position 334 to 969 of SEQ ID NO:3;
(E) a nucleotide sequence consisting of the nucleotide position 334 to 969 of SEQ ID NO:3 wherein one or several nucleotides are deleted, substituted or added, which encodes a protein having cysteine at position 152 and having a dual specificity phosphatase activity; and
(F) a nucleotide sequence hybridizing to a nucleotide sequence consisting of the nucleotide position 334 to 969 of SEQ ID NO:3 under stringent conditions, which encodes a protein having cysteine at position 152 and having a dual specificity phosphatase activity; and
(IV) a recombinant vector comprising a DNA encoding a protein consisting of any one of the following amino acid sequences and capable of expressing a protein having an inhibitory activity against a dual specificity phosphatase:

(a) an amino acid sequence wherein cysteine at position 138 is substituted with another amino acid in the amino acid sequence of SEQ ID NO:2;
(b) an amino acid sequence wherein cysteine at position 138 is substituted with another amino acid and one or several amino acids other than cysteine at position 138 are deleted, substituted or added in the amino acid sequence of SEQ ID NO:2, wherein a protein consisting of the amino acid sequence has an inhibitory activity against a dual specificity phosphatase; and
c) an amino acid sequence having at least 60% or more homology to the amino acid sequence of SEQ ID NO: 2 and having at position 138 an amino acid other than cysteine, wherein a protein consisting of the amino acid sequence has an inhibitory activity against a dual specificity phosphatase.

An inhibitory agent for cardiomyocyte differentiation of the present invention is not particularly limited as long as it comprises any one of the following proteins (V), following fusion proteins (VI), or following recombinant vectors (VII) or (VIII):

(V) a protein consisting of any one of the following amino acid sequences:
(A) the amino acid sequence of SEQ ID NO:2;
(B) an amino acid sequence wherein one or several amino acids except for cysteine at position 138 are deleted, substituted or added in the amino acid sequence of SEQ ID NO:2, wherein a protein consisting of the amino acid sequence has a dual specificity phosphatase activity;
(C) an amino acid sequence having at least 60% or more homology to the amino acid sequence of SEQ ID NO:2 and having cysteine at position 138, wherein a protein consisting of the amino acid sequence has a dual specificity phosphatase activity;
(a) an amino acid sequence wherein cysteine at position 152 is substituted with another amino acid in the amino acid sequence of SEQ ID NO:4;
(b) an amino acid sequence wherein cysteine at position 152 is substituted with another amino acid and one or several amino acids other than cysteine at position 152 are deleted, substituted or added in the amino acid sequence of SEQ ID NO:4, wherein a protein consisting of the amino acid sequence has an inhibitory activity against a dual specificity phosphatase; and
(c) an amino acid sequence having at least 60% or more homology to the amino acid sequence of SEQ ID NO: 4 and having at position 152 an amino acid other than cysteine, wherein a protein consisting of the amino acid sequence has an inhibitory activity against a dual specificity phosphatase;
(VI) a fusion protein wherein any one of the proteins of the above (V) is linked with a marker protein and/or a peptide tag;
(VII) a recombinant vector comprising a DNA consisting of any one of the following nucleotide sequences and capable of expressing a protein having a dual specificity phosphatase activity:
(A) a nucleotide sequence encoding a protein consisting of the amino acid sequence of SEQ ID NO:2;
(B) a nucleotide sequence encoding a protein consisting of an amino acid sequence wherein one or several amino acids except for cysteine at position 138 are deleted, substituted or added in the amino acid sequence of SEQ ID NO:2, wherein the protein has a dual specificity phosphatase activity;
(C) a nucleotide sequence encoding a protein consisting of an amino acid sequence having at least 60% or more homology to the amino acid sequence of SEQ ID NO:2 and having cysteine at position 138, wherein the protein has a dual specificity phosphatase activity;

(D) a nucleotide sequence consisting of the nucleotide position 78 to 674 of SEQ ID NO:1;
(E) a nucleotide sequence consisting of the nucleotide position 78 to 674 of SEQ ID NO:1 wherein one or several nucleotides are deleted, substituted or added, which encodes a protein having cysteine at position 138 and having a dual specificity phosphatase activity; and
(F) a nucleotide sequence hybridizing to a nucleotide sequence consisting of the nucleotide position 78 to 674 of SEQ ID NO:1 under stringent conditions, which encodes a protein having cysteine at position 138 and having a dual specificity phosphatase activity; and
(VIII) a recombinant vector comprising a DNA encoding a protein consisting of any one of the following amino acid sequences and capable of expressing a protein having an inhibitory activity against a dual specificity phosphatase:
(a) an amino acid sequence wherein cysteine at position 152 is substituted with another amino acid in the amino acid sequence of SEQ ID NO:4;
(b) an amino acid sequence wherein cysteine at position 152 is substituted with another amino acid and one or several amino acids other than cysteine at position 152 are deleted, substituted or added in the amino acid sequence of SEQ ID NO:4, wherein a protein consisting of the amino acid sequence has an inhibitory activity against a dual specificity phosphatase; and
(c) an amino acid sequence having at least 60% or more homology to the amino acid sequence of SEQ ID NO: 4 and having at position 152 an amino acid other than cysteine, wherein a protein consisting of the amino acid sequence has an inhibitory activity against a dual specificity phosphatase.

A regulator of cardiomyocyte differentiation of the present invention (a promoting agent and inhibitory agent for differentiation) may comprise any component in addition to the above-described essential component as long as it does not hamper the effect of the present invention. A regulator of cardiomyocyte differentiation of the present invention (a promoting agent and inhibitory agent for differentiation) is expected to be applied to a prophylactic agent and therapeutic agent for cardiomyocyte differentiation-related heart diseases.

A method for using a promoting agent for cardiomyocyte differentiation or an inhibitory agent for cardiomyocyte differentiation of the present invention is not particularly limited as long as promoting effect or inhibitory effect for cardiomyocyte differentiation is obtained. For example, these can be used by introducing a recombinant vector of the above (III) or (IV) contained in these agents into a cardiomyocyte and expressing a protein of the above (I) or a fusion protein of the above (II) in the cardiomyocyte.

As a cardiomyocyte herein, human or non-human mammalian cardiomyocyte can be preferably exemplified. More preferred specific examples of a non-human mammal include one or more selected from the group consisting of mouse, rat, guinea pig, hamster, rabbit, cat, dog, sheep, pig, goat, bovine and monkey.

A method of screening for a substance that promotes or inhibits cardiomyocyte differentiation of the present invention is not particularly limited as long as the method comprises the step of culturing in the presence of a test substance a transformed cardiomyocyte into which a recombinant vector of the present invention is introduced, which expresses a protein of the present invention, and measuring and evaluating the degree of the cardiomyocyte differentiation. More specifically, the method comprises the steps of culturing in the presence of a test substance a transformed cardiomyocyte into which a recombinant vector of the present invention is introduced, which expresses a protein of the present invention, and measuring the degree of the cardiomyocyte differentiation, and comparing the degree of the cardiomyocyte differentiation with that of said transformed cardiomyocyte cultured in the absence of said test substance and evaluating the effect of said test substance to the cardiomyocyte differentiation. Herein, the term cardiomyocyte refers to animal cardiomyocyte, preferably animal cardiomyocyte wherein differentiation is not completed, e.g., animal fetal cardiomyocyte. Preferably, animal is mammal. Among mammals, human, mouse, rat, and rabbit are more preferred. A transformant used in the method of screening is a transformed animal. As an animal for a transformed animal, human or non-human mammal is preferred. Among non-human mammals, one or more selected from the group consisting of mouse, rat, guinea pig, hamster, rabbit, cat, dog, sheep, pig, goat, bovine and monkey can be more preferably exemplified.

A method of screening for a substance that promotes or suppresses cardiomyocyte differentiation of the present invention also includes a method for evaluating a substance that promotes or suppresses cardiomyocyte differentiation. For example, use of a substance known to promote or suppress cardiomyocyte differentiation as a test substance is also included.

The degree of differentiation can be determined by examining the expression level of any one or more proteins of MyHC (Myosin Heavy Chain), Myogenin, and Troponin T. All of these proteins, MyHC (Myosin Heavy Chain), Myogenin, and Troponin T tend to increase in expression level as differentiation proceeds. For other animals besides rat, an activity to promote or suppress cardiomyocyte differentiation can be easily confirmed by a similar method.

Whether a test substance has an activity to promote cardiomyocyte differentiation or not can be easily examined by confirming that when cardiomyocyte is cultured under suitable conditions which are the same conditions except the presence or absence of the test substance, one cultured in the presence of the test substance shows more rapid differentiation. Further, whether a test substance has an activity to suppress cardiomyocyte differentiation or not can be easily examined by confirming that when cardiomyocyte is cultured under suitable conditions which are the same conditions except the presence or absence of the test substance, one cultured in the presence of the test substance shows retarded differentiation.

Further, a method of screening for a substance that promotes or suppresses cardiomyocyte differentiation of the present invention is expected to be applied to a method of screening for a possible substance for a prophylactic agent and therapeutic agent for cardiomyocyte differentiation-related heart diseases.

Further, the following DNAs (IX) of the present invention can be used for preparing a protein having a dual specificity phosphatase activity.
(IX) a DNA consisting of any one of the following nucleotide sequences:
(A) a nucleotide sequence encoding a protein consisting of the amino acid sequence of SEQ ID NO:2;
(B) a nucleotide sequence encoding a protein consisting of an amino acid sequence wherein one or several amino acids except for cysteine at position 138 are deleted, substituted or added in the amino acid sequence of SEQ ID NO:2, wherein the protein has a dual specificity phosphatase activity;
(C) a nucleotide sequence encoding a protein consisting of an amino acid sequence having at least 60% or more homology to the amino acid sequence of SEQ ID NO:2 and having cysteine at position 138, which protein has a dual specificity phosphatase activity;
(D) a nucleotide sequence consisting of the nucleotide position 78 to 674 of SEQ ID NO:1;
(E) a nucleotide sequence consisting of the nucleotide position 78 to 674 of SEQ ID NO:1 wherein one or several nucleotides are deleted, substituted or added, which encodes a protein having cysteine at position 138 and having a dual specificity phosphatase activity;
(F) a nucleotide sequence hybridizing to a nucleotide sequence consisting of the nucleotide position 78 to 674 of SEQ ID NO:1 under stringent conditions, which encodes a protein having cysteine at position 138 and having a dual specificity phosphatase activity;
(A) a nucleotide sequence encoding a protein consisting of the amino acid sequence of SEQ ID NO:4;
(B) a nucleotide sequence encoding a protein consisting of an amino acid sequence wherein one or several amino acids except for cysteine at position 152 are deleted, substituted or added in the amino acid sequence of SEQ ID NO:4, wherein the protein has a dual specificity phosphatase activity;
(C) a nucleotide sequence encoding a protein consisting of an amino acid sequence having at least 60% or more homology to the amino acid sequence of SEQ ID NO:4 and having cysteine at position 152, wherein the protein has a dual specificity phosphatase activity;
(D) a nucleotide sequence consisting of nucleotide 334 to 969 of SEQ ID NO:3;
(E) a nucleotide sequence consisting of the nucleotide position 334 to 969 of SEQ ID NO:3 wherein one or several nucleotides are deleted, substituted or added, which encodes a protein having cysteine at position 152 and having a dual specificity phosphatase activity; and
(F) a nucleotide sequence hybridizing to a nucleotide sequence consisting of the nucleotide position 334 to 969 of SEQ ID NO:3 under stringent conditions, which encodes a protein having cysteine at position 152 and having a dual specificity phosphatase activity.

Further, the following DNAs (X) of the present invention can be used for preparing a protein having an inhibitory activity against a dual specificity phosphatase:
(X) a DNA encoding a protein consisting of any one of the following amino acid sequences:
(a) an amino acid sequence wherein cysteine at position 138 is substituted with another amino acid sequence in the amino acid sequence of SEQ ID NO:2;
(b) an amino acid sequence wherein cysteine at position 138 is substituted with another amino acid and one or several amino acids other than cysteine at position 138 are deleted, substituted or added in the amino acid sequence of SEQ ID NO:2, wherein a protein consisting of the amino acid sequence has an inhibitory activity against a dual specificity phosphatase;
(c) an amino acid sequence having at least 60% or more homology to the amino acid sequence of SEQ ID NO: 2 and having at position 138 an amino acid other than cysteine, wherein a protein consisting of the amino acid sequence has an inhibitory activity against a dual specificity phosphatase;
(a) an amino acid sequence wherein cysteine at position 152 is substituted with another amino acid in the amino acid sequence of SEQ ID NO:4;
(b) an amino acid sequence wherein cysteine at position 152 is substituted with another amino acid and one or several amino acids other than cysteine at position 152 are deleted, substituted or added in the amino acid sequence of SEQ ID NO:4, wherein a protein consisting of the amino acid sequence has an inhibitory activity against a dual specificity phosphatase; and
(c) an amino acid sequence having at least 60% or more homology to the amino acid sequence of SEQ ID NO:4 and having at position 152 an amino acid other than cysteine, wherein a protein consisting of the amino acid sequence has an inhibitory activity against a dual specificity phosphatase.

Further, the present invention also includes a method for activating promotion of cardiomyocyte differentiation by using a protein having an activity to promote cardiomyocyte differentiation of the present invention and includes a method for activating suppression of cardiomyocyte differentiation by using a protein having an activity to suppress cardiomyocyte differentiation of the present invention.

Further, the present invention also includes a method for preparing a dephosphorylated amino acid from a phosphorylated amino acid by using a protein having a dual specificity phosphatase activity of the present invention.

Further, an antibody of the present invention is not particularly limited as long as the antibody specifically binds to any of the proteins of the present invention such as DUSP13 and DUSP26. Specific examples of an antibody specifically binds to any of the proteins of the present invention (hereinafter referred to as a "protein of the present invention") include immunospecific antibodies such as a monoclonal antibody, polyclonal antibody, chimeric antibody, single-chain antibody and humanized antibody. These antibodies can be generated using a protein of the present invention as an antigen according to a conventional method. Among these, monoclonal antibody is preferred for its specificity. Such antibodies and the like that specifically bind to a protein of the present invention are useful, for example, for diagnosing a disease originated from mutation or deletion in a protein of the present invention and for elucidating a molecular mechanism of a protein of the present invention.

An antibody against a protein of the present invention can be produced by administering the protein or an epitope-containing fragment thereof, or cells expressing the protein on the membrane surfaces to an animal (preferably a non-human animal) by a conventional protocol. Furthermore, any method can be used for the preparation of a monoclonal antibody, the method including hybridoma method (Nature 256, 495-497, 1975), trioma method, human B cell hybridoma method (Immunology Today 4, 72, 1983), and EBV-hybridoma method (MONOCLONAL ANTIBODIES AND CANCER THERAPY, pp. 77-96, Alan R. Liss, Inc., 1985), which methods provide antibodies produced by the culture of a continuous cell line.

Further, to prepare a single-chain antibody against a protein of the present invention, the method for preparing a single-chain antibody (U.S. Pat. No. 4,946,778) can be applied. Further, transgenic mouse or other mammals can be used to express a humanized antibody, which can be used to isolate and identify a clone expressing the protein and to purify the polypeptide through affinity chromatography. An antibody against a protein of the present invention is useful for elucidation of a molecular mechanism of a protein of the present invention.

Further, functional analysis of the above protein of the present invention can be attained by using an antibody such as a monoclonal antibody against a protein of the present invention which is labeled with, for example, a fluorescent substance such as FITC (fluorescein isocyanate) or tetramethyl rhodamine isocyanate, a radioisotope such as 125I, 32P, 14C, 35S or 3H, or an enzyme such as alkaline phosphatase, peroxidase, β-galactosidase or phycoerythrin, or by using an antibody which is a fusion protein fused with a fluorescence emission protein such as green fluorescent protein. Further, examples of immunoassay include RIA method, ELISA method, fluorescent antibody method, plaque method, spot method, hemagglutination method and Ouchterlony method.

The term "bind to a protein of the present invention" means that the antibody has an ability to bind to a protein of the present invention with an equilibrium dissociation constant KD from $10^{-7}$ to $10^{-10}$ M. The equilibrium dissociation constant KD of an antibody produced by a method of the present invention or a fragment thereof can be determined by any appropriate method selected by those skilled in the art.

The present invention will be described in more detail with reference to the Examples. The technical scope of the present invention should not be restricted by these exemplification.

EXAMPLES

1. Test for In Vitro Dephosphorylation Activity

Figure 1:
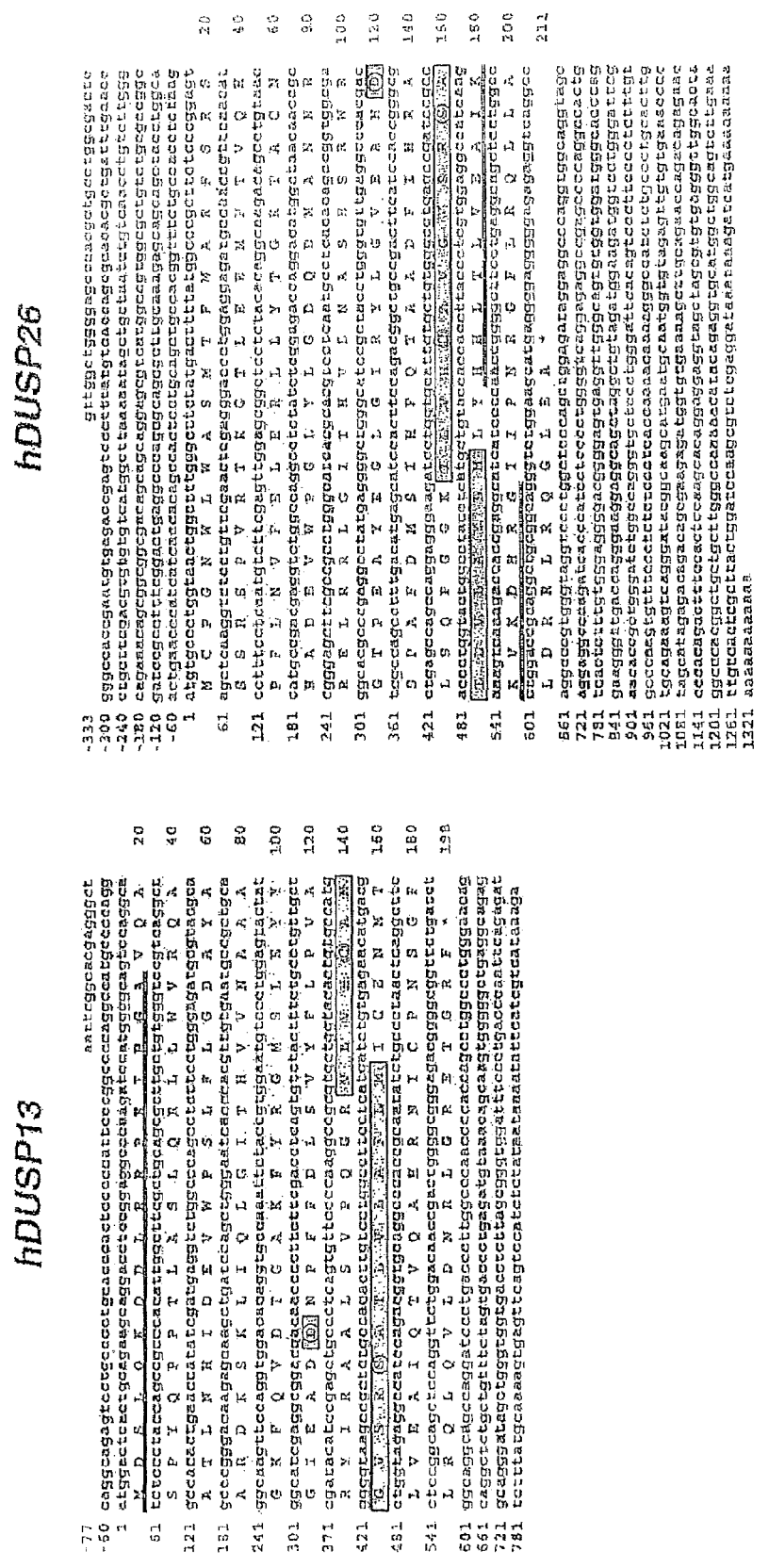
Figure 2:
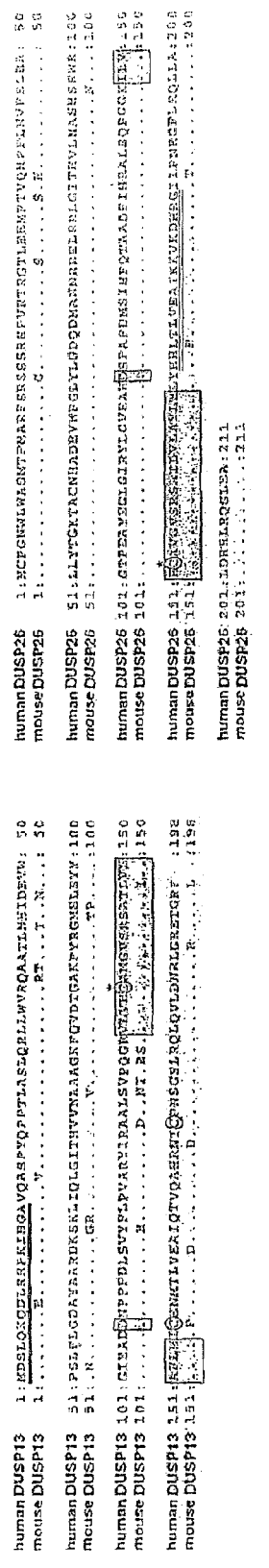

PCR was carried out using cDNA from human HeLa cell or human tissue as a template to clone a gene encoding human DUSP13 and a gene encoding human DUSP26. As the primers for the gene encoding human DUSP13, the oligonucleotide consisting of the nucleotide sequence of SEQ ID NO:5 and the oligonucleotide consisting of the nucleotide sequence of SEQ ID NO:6 were used. Further, as the primers for the gene encoding human DUSP26, the oligonucleotide consisting of the nucleotide sequence of SEQ ID NO:7 and the oligonucleotide consisting of the nucleotide sequence of SEQ ID NO:8 were used. The PCR was carried out using High Fidelity DNA polymerase KOD-Plus-(TOYOBO Co., Ltd.) with 35 cycles of 98° C. for 15 seconds, 55° C. for 30 seconds, and 68° C. for 1 minute (Gene Amp PCR System, PerkinElmer). In this way, human DUSP13 (hDUSP13) and human DUSP26 (hDUSP26) were cloned. The amino acid sequences are shown in SEQ ID NO:2 and SEQ ID NO:4, respectively. Furthermore, catalytic domains of dephosphorylation enzymes, human DUSP13 and human DUSP26, are shown in gray boxes in FIG. 1 and FIG. 2, respectively. These catalytic domains are conserved as hitherto reported DSPs. In these figures, sequences of each peptide used to immunize a rabbit for the preparation of an antibody is shown (FIG. 1 and FIG. 2, double-underline).

To confirm a dephosphorylation enzyme activity of human DUSP13 and human DUSP26 proteins, experiments were carried out as follows.

Each of the DNA encoding human DUSP13 protein and the DNA encoding human DUSP26 protein obtained through the above-described PCR was ligated into pGEX vector (Amersham Biosciences), which vector has a GST gene. The vector was transformed into *E. coli* and the GST (glutathione S-transferase) fusion protein was expressed in *E. coli*. These fusion proteins were affinity-purified by using glutathione Sepharose 4B (Amersham Biosciences). In this way, human DUSP13 protein and human DUSP26 protein were purified.

In addition, DNA encoding the human DUSP13 protein wherein cysteine at position 138 is substituted with serine was generated by site-directed mutagenesis. This DNA was ligated into pGEX vector, which was then transformed into *E. coli* to express GST (glutathione S-transferase) fusion protein in *E. coli*. This fusion protein was affinity-purified by using glutathione Sepharose 4B (Amersham Biosciences). In this way, the human DUSP13 protein wherein cysteine at position 138 is substituted with serine (hereinafter referred to as "DUSP13 C138S protein") was purified. By the same method, the human DUSP26 protein wherein cysteine at position 152 is substituted with serine (hereinafter referred to as "DUSP26 C152S protein") was purified.

Dephosphorylation enzyme activities of human DUSP13 protein, human DUSP26 protein, DUSP13 C138S protein, and DUSP26 C152S protein, which were obtained by the purification, were measured using para-nitrophenyl phosphate (pNPP) as a substrate. In addition, the same dephosphorylation enzyme activity test was performed with the addition of sodium vanadate (Vanadate), a tyrosine dephosphorylation enzyme inhibitor, in addition to para-nitrophenyl phosphate. The results are shown in FIG. 3. In the figure, DUSP19 is a human DUSP protein that the present inventors previously isolated.

As known from the results shown in FIG. 3, upper left and upper center, dephosphorylation enzyme activity was detected in time-dependent and dose-dependent manner for human DUSP13 protein and human DUSP26 protein (hereinafter referred to as "wild-type protein"). In contrast, dephosphorylation enzyme activity was not observed for DUSP13 C138S protein and DUSP26 C152S protein (hereinafter referred to as "CS mutant protein"). Further, dephosphorylation enzyme activity was not observed even for the wild-type proteins in the presence of a tyrosine dephosphorylation enzyme inhibitor, sodium vanadate (1 mM concentration; Vanadate). This suggested that the CS mutant proteins can have a function of dominant negative enzyme as an enzyme activity-deficient protein.

Further, to show that, among dephosphorylation enzymes, human DUSP13 protein is DSP (Dual Specificity Phosphatase), which dephosphorylates a phosphate group of phosphorylated tyrosine, phosphorylated serine and phosphorylated threonine, ERK2 protein or MEK1 protein was used as a substrate. When activated, ERK2 protein is phosphorylated simultaneously at known tyrosine and threonine, and MEK1 protein is phosphorylated at a serine.

DNA encoding ERK2 was fused with DNA encoding GST tag and subcloned into a vector. The vector was transformed into HeLa cells to express the GST-ERK2 protein. After eight hours of serum removal, the cells were treated with phorbol ester (Treatment), which is known to activate ERK2, to simultaneously phosphorylate known tyrosine and threonine in GST-ERK2 protein. This GST-ERK2 protein was precipitated with glutathione Sepharose, and was assayed at 37° C. for 60 minutes in a buffer with or without the addition of a predetermined amount of human DUSP13 protein. After the assay, SDS-polyacrylamide gel electrophoresis (SDS-PAGE) was carried out, followed by western blotting using anti-phosphorylated threonine antibody, detecting the degree of dephosphorylation of a specific threonine (Thr) residue in GST-ERK2 protein. (see FIG. 3, lower left, top panel). The same experiment was carried out using anti-phosphorylated tyrosine antibody in place of anti-phosphorylated threonine antibody to detect the degree of dephosphorylation of a specific tyrosine (Tyr) residue in GST-ERK2 protein (see FIG. 3, lower left, second panel from the top). Further, the same experiment was carried out using anti-phosphorylated ERK antibody which recognizes both threonine residue and tyrosine residue that are phosphorylated when ERK is activated, which confirmed that the degree of dephosphorylation of these residues hardly depends on the concentration of human DUSP13 protein (see FIG. 3, lower left, third panel from the top). Further, the same experiment was performed using anti-ERK antibody in place of anti-phosphorylated threonine antibody (see FIG. 3, lower left, fourth panel from the top), which confirmed that all the lanes contained about the same amount of GST-ERK2 protein. The leftmost lane was not treated with phorbol ester, which is known to activate ERK2, and the comparison with the other lanes shows lower degree of phosphorylation of tyrosine and threonine in non-activated ERK2.

DNA encoding MEK1 was fused with DNA encoding HA tag and subcloned into a vector. The vector was transformed into HeLa cells to express HA-MEK1 protein. The cells were stimulated with serum (Serum) which is known to activate MEK1, phosphorylating the serine (Ser) residue at position 217 of HA-MEK1 protein. This HA-MEK1 protein was immunoprecipitated (IP) with anti-Ha antibody (anti-HA), and was assayed at 37° C. for 60 minutes in a buffer with or without the addition of a predetermined amount of human DUSP13 protein. After the assay, SDS-polyacrylamide gel electrophoresis (SDS-PAGE) was carried out, followed by western blotting using anti-phosphorylated MEK1/2 antibody which detects the phosphorylation of the above-mentioned serine residue, detecting the degree of the dephosphorylation of the specific serine residue in HA-MEK1 protein (see FIG. 3, lower center, top panel). The leftmost lane was not stimulated with serum, which is known to activate MEK1, and comparison with the other lanes shows lower degree of phosphorylation of the serine in non-activated MEK1.

2. Test for In Vivo Dephosphorylation Activity

Figure 4:
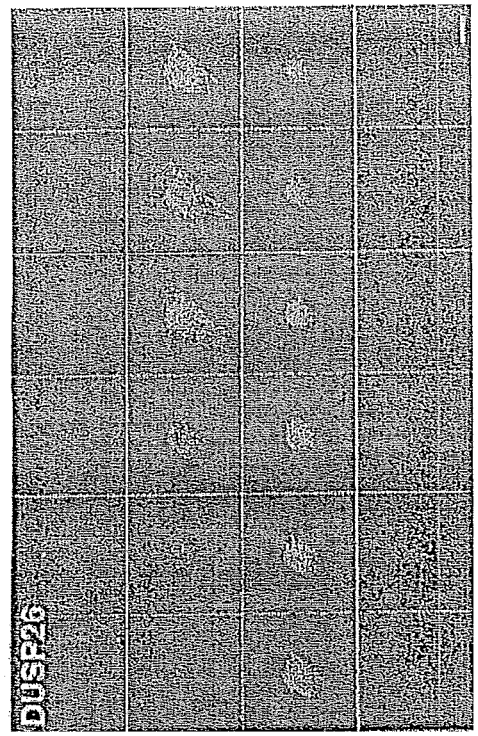
FIG. 4 shows the subcellular localization of human DUSP13 protein (upper left and lower left) and human DUSP26 protein (upper right).
Figure 4:
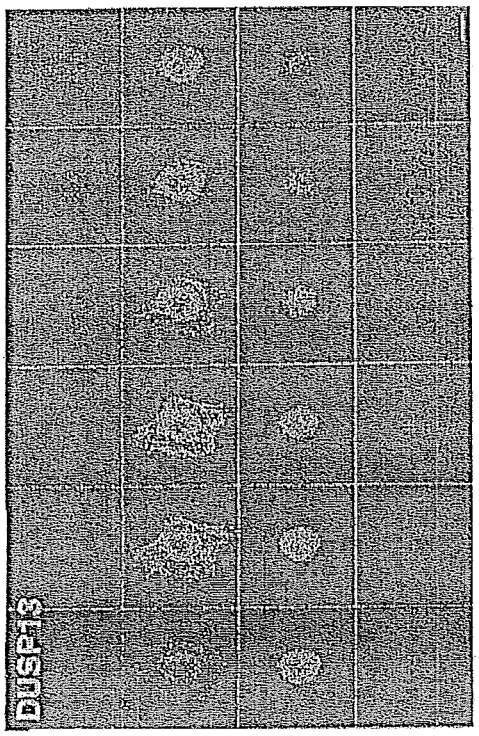
Figure 4:
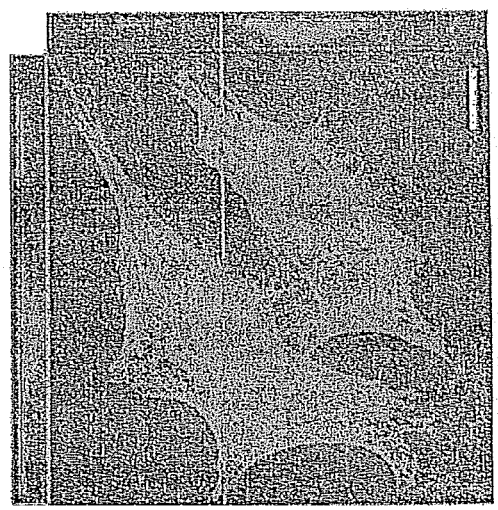

To confirm whether human DUSP13 protein and human DUSP26 protein can have dephosphorylation enzyme activity in a cell as well, their subcellular localizations were investigated first. DNA encoding human DUSP13 protein having Myc tag at its N terminus was subcloned into a mammalian expression vector (pME vector), which was then introduced into HeLa cells to transiently express the recombinant protein. Ten hours after the DNA introduction, the cells were fixed with 4% paraformaldehyde at room temperature for 15 minutes. Then, the membrane was permeabilized with 0.2% Triton X-100. After the permeabilization treatment, the cells were reacted with anti-Myc antibody (9E10) as a primary antibody, washed, and reacted with FITC (fluorescein isothiocyanate)-labeled anti-mouse IgG secondary antibody for cellular immunostaining. The immunostained cells were studied under a confocal microscope to investigate the localization of human DUSP13 protein. Further, DNA encoding human DUSP26 protein having Myc tag at its N terminus was subcloned into a mammalian expression vector (pME vector), which was then introduced into HeLa cells to transiently express the recombinant protein. In the same manner as described above, ten hours after the DNA introduction, the cells were reacted with anti-Myc antibody (9E10) as a primary antibody, washed, and reacted with FITC-labeled anti-mouse IgG secondary antibody for cellular immunostaining. The immunostained cells were studied under a confocal microscope to investigate the localization of human DUSP26 protein. These results are shown in the left part of FIG. 4 and FIG. 5. The lower left part of FIG. 4 shows the above-described HeLa cells transiently expressing DUSP13, wherein DUSP13 was immunostained with FITC-labeled anti-mouse IgG secondary antibody and the cells were immunostained with rhodamine-labeled phalloidin (INVITROGEN) at the same time. Phalloidin binds to actin, representing the localization to cell membrane, which is observed as red fluorescent image of rhodamine in this experiment. Thus, when overlapped with green, which represents the localization of DUSP13, it appears to be yellow. In the lower left part of FIG. 4, the nucleus appeared to be green and the cell membrane to be yellow.

Figure 5:
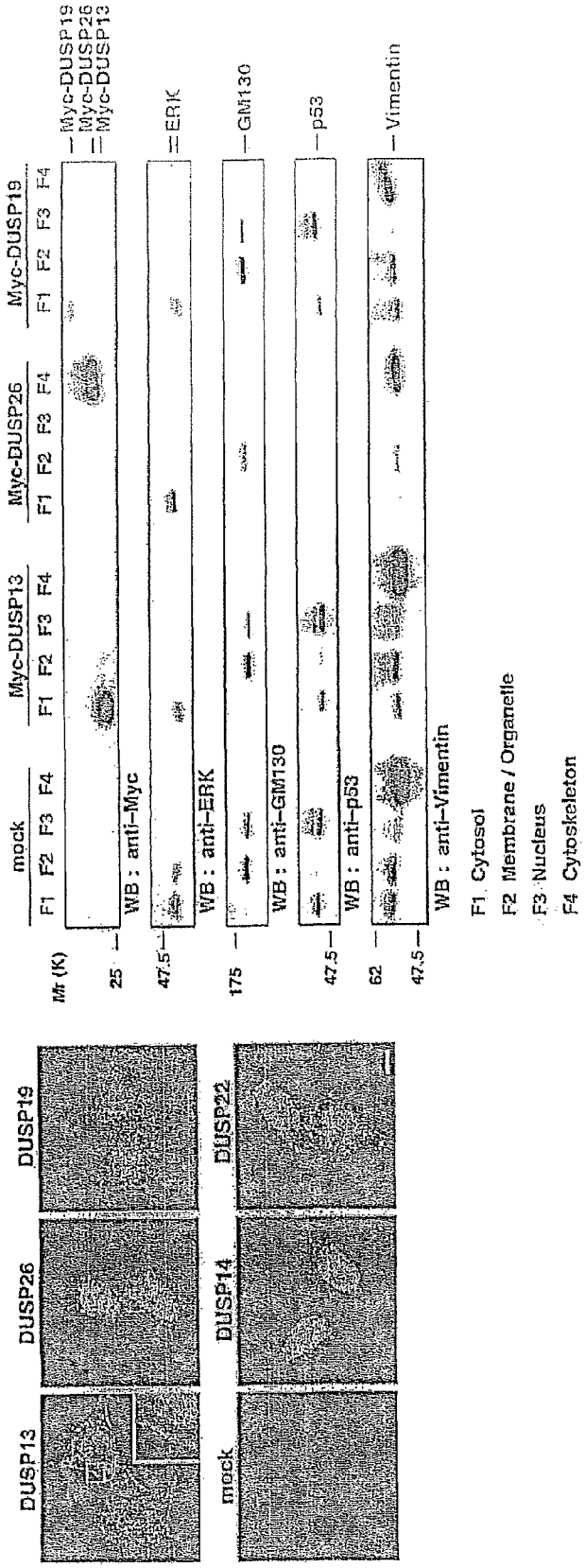

As known from the left part of FIG. 4 and FIG. 5, human DUSP13 protein was observed to be localized around the nucleus and to the cell membrane, and human DUSP26 protein to and around the nucleus.

3. Test for Dephosphorylation Activity of Human DUSP13 and Human DUSP26 in Subcellular Fractions Next, cell extracts from each of the both cells expressing each of the above-described recombinant proteins were fractionated into cytosol, membrane/organelles, nucleus, and cytoskeletons. Each of the obtained samples was subjected to SDS-polyacrylamide gel electrophoresis (SDS-PAGE) and the subcellular fractions were detected by western blotting using anti-Myc antibody. The results are shown in FIG. 5 (right, top panel).

As known from FIG. 5 (right, top panel), human DUSP13 protein was observed to exist in the cytosol fraction (F1: Cytosol) and in the membrane/organelles fraction (F2: Membrane/Organelle), while human DUSP26 protein was observed to exist in the cytoskeleton fraction (F4: Cytoskeleton).

Further, DNA encoding human DUSP13 protein or human DUSP26 protein having EGFP (Enhanced Green Fluorescent Protein) tag at its N terminus was subcloned into a mammalian expression vector (pEGFP-C3; Clontech Laboratories Inc.), which was then introduced into HeLa cells. After the introduction, the cells were cultured on a selection medium containing 750 µg/ml of G418 for three weeks to generate stably expressing cell lines for each protein (GFP-DUSP13/HeLa and GFP-DUSP26/HeLa) and some clones were obtained. In the same manner, stably expressing cell lines for a mutated protein of DUSP13 in which cysteine (Cys) at position 138 is substituted with serine (Ser) and a mutated protein of DUSP26 in which cysteine (Cys) at position 152 is substituted with serine (Ser) were generated (GFP-DUSP13 C138S/HeLa and GFP-DUSP26 C152S/HeLa). After that, these subcellular localization and subcellular fractionation were investigated and the results were similar to that shown in FIG. 4 and FIG. 5.

Figure 6:
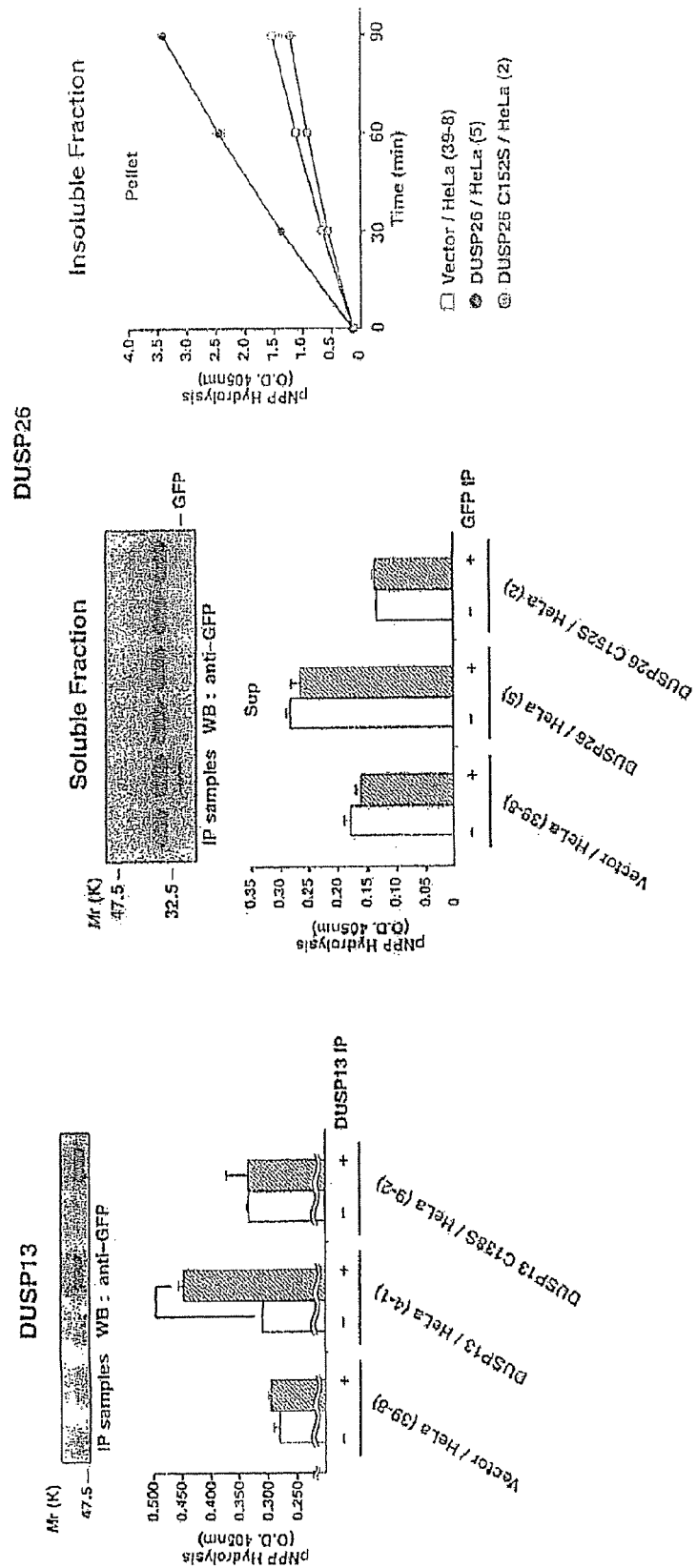
FIG. 6 shows dephosphorylation activity of human DUSP13 in the soluble fraction of stably expressing cells (left), dephosphorylation activity of human DUSP26 in the soluble fraction of stably expressing cells (center), and dephosphorylation activity of human DUSP26 in the insoluble fraction of stably expressing cells (right).

4. Test for Dephosphorylation Activity of Stably Expressing Cells of Human DUSP13 or Human DUSP26 in the Subcellular Fractions Next, these stably expressing cell lines GFP-DUSP13/HeLa, GFP-DUSP26/HeLa, GFP-DUSP13 C138S/HeLa, and GFP-DUSP26 C152S/HeLa were used to test the dephosphorylation enzyme activity of the expressed proteins in the subcellular fractions. Clone number for each of the generated stably expressing cell lines is shown in parentheses. For GFP-DUSP13/HeLa (DUSP13/HeLa (4-1)) and GFP-DUSP13 C138S/HeLa (DUSP13 C138S/HeLa (9-2)), expressed subcellular proteins thereof were immunoprecipitated from the stably expressing cell lines by using anti-DUSP13 antibody (IP: immunoprecipitation), and dephosphorylation enzyme activities thereof were measured using para-nitrophenyl phosphate (pNPP) as a substrate. As a result, the enzymatic activity of the immunoprecipitates with anti-DUSP13 antibody from DUSP13/HeLa(4-1) showed a higher dephosphorylation enzyme activity than that of the immunoprecipitates from Vector/HeLa and DUSP13 C138S/HeLa (9-2). This suggested that DUSP13 protein has its enzymatic activity in a cell as well (FIG. 6, left). Further, when DUSP13 C138S/HeLa was used, significant difference in dephosphorylation enzyme activity was not observed between the cases where the immunoprecipitation using anti-DUSP13 antibody was carried out (DUSP13 IP+) and where the immunoprecipitation using anti-DUSP13 antibody was not carried out (DUSP13 IP−), which is the same as when vector/HeLa was used. This revealed that DUSP13 C138S did not have dephosphorylation activity in a cell either (FIG. 6, left).

In addition, a sample that is immunoprecipitated (IP) with anti-GFP antibody (GFP IP+) and a sample that is not immunoprecipitated with the antibody (GFP IP−) were prepared for each Triton-soluble fraction of vector/HeLa, GFP-DUSP26/HeLa (DUSP26/HeLa(5)), and GFP-DUSP26 C152S/HeLa (DUSP26 C152S/HeLa(2)). Then, each of these samples was measured for its dephosphorylation enzyme activity by using para-nitrophenyl phosphate (pNPP) as a substrate. As a result, no difference was observed in dephosphorylation enzyme activity between the samples that were immunoprecipitated with anti-GFP antibody and the samples that were not immunoprecipitated in any of the cell samples (see FIG. 6, lower center panel), which indicated that a subcellular dephosphorylation enzyme activity was not observed in the soluble fractions in any of the cells. Next, these samples were subjected to western blotting using anti-GFP antibody, showing a specific band below 32.5 K (see FIG. 6, center, upper panel, second lane). This 32.5-K band was detected only in Vector/HeLa, indicating the expression of EGFP itself. On the other hand, a band around 47.5 K that indicates EGFP-added DUSP26 was not detected in the other samples. This revealed that DUSP26 does not exist in the soluble fraction of either of DUSP26/HeLa(5) or DUSP26 C152S/HeLa(2) in consistent with the above-described results.

Accordingly, to the Triton-insoluble fraction in which DUSP26 expression was observed, para-nitrophenyl phosphate (pNPP) was added as a substrate to measure the dephosphorylation enzyme activity. As a result, the higher dephosphorylation enzyme activity was detected in the insoluble fraction of DUSP26/HeLa(5) as compared to that in the insoluble fraction of Vector/HeLa or DUSP26 C152S/HeLa (2) (FIG. 6, right). This results and the results of subcellular fractionation of DUSP26 (FIG. 5) suggested that DUSP26 has its activity on cytoskeleton.

5. mRNA Expression of Human DUSP13, Human DUSP26 or the Like in Each Tissue

Figure 7:
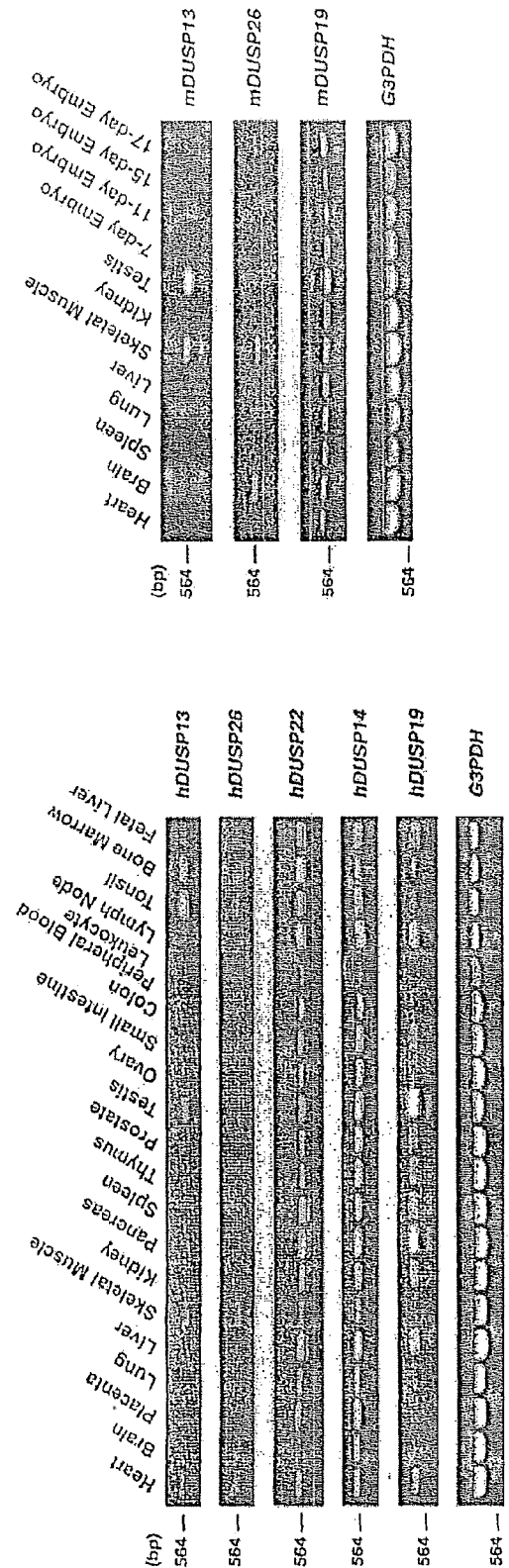
FIG. 7 shows the mRNA expression of human DUSP13, human DUSP26 or the like in various tissues.
Figure 8:
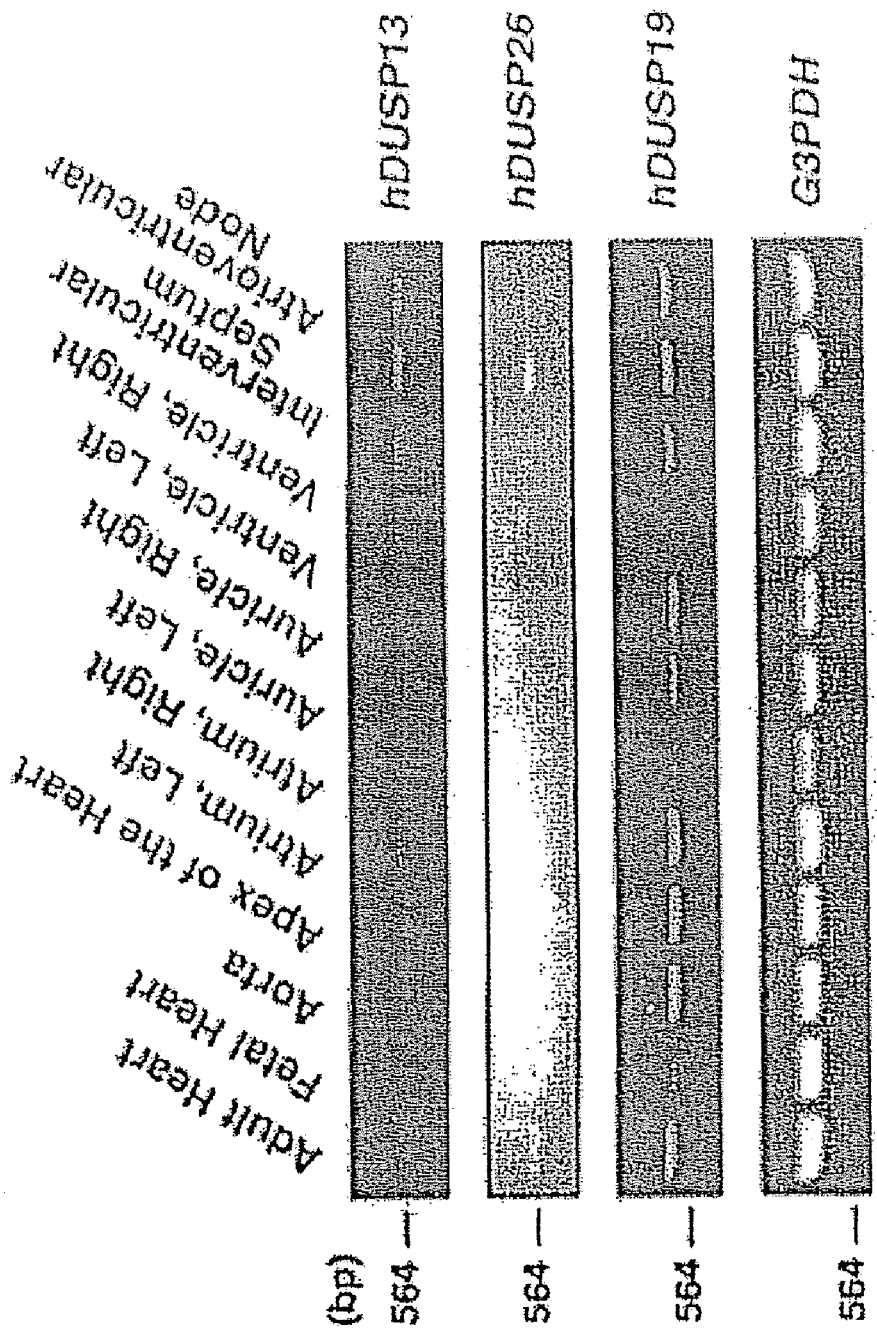
FIG. 8 shows the mRNA expression of human DUSP13, human DUSP26 or the like in human heart.

First-strand cDNA from each tissue was PCR-amplified with specific primers, and expression level of each mRNA in each human or mouse tissue was detected by semiquantitative PCR using G3PDH as an internal standard. As a result, in human, expression of all of each mRNA was observed in heart (FIG. 7, left), while, in mouse, expression of each mRNA was not detected in heart and showed clear tissue specificity (FIG. 7, right). On the other hand, mRNAs for hDUSP22, hDUSP14 and hDUSP19, which had been previously isolated by the present inventors, did not show tissue specificity (FIG. 7). Furthermore, all of each mRNA in human heart showed a higher expression in adult than fetus (FIG. 8). The hDUSP13 expression was observed in the right and left atria, auricles, and ventricles, interventricular septum, and atrioventricular node, while the hDUSP26 expression was observed only in apex of the heart, left atrium, and interventricular septum and clear expression was not observed in right and left ventricles (FIG. 8).

6. Endogenous Expression of DUSP13 at the Protein Level

Figure 9:
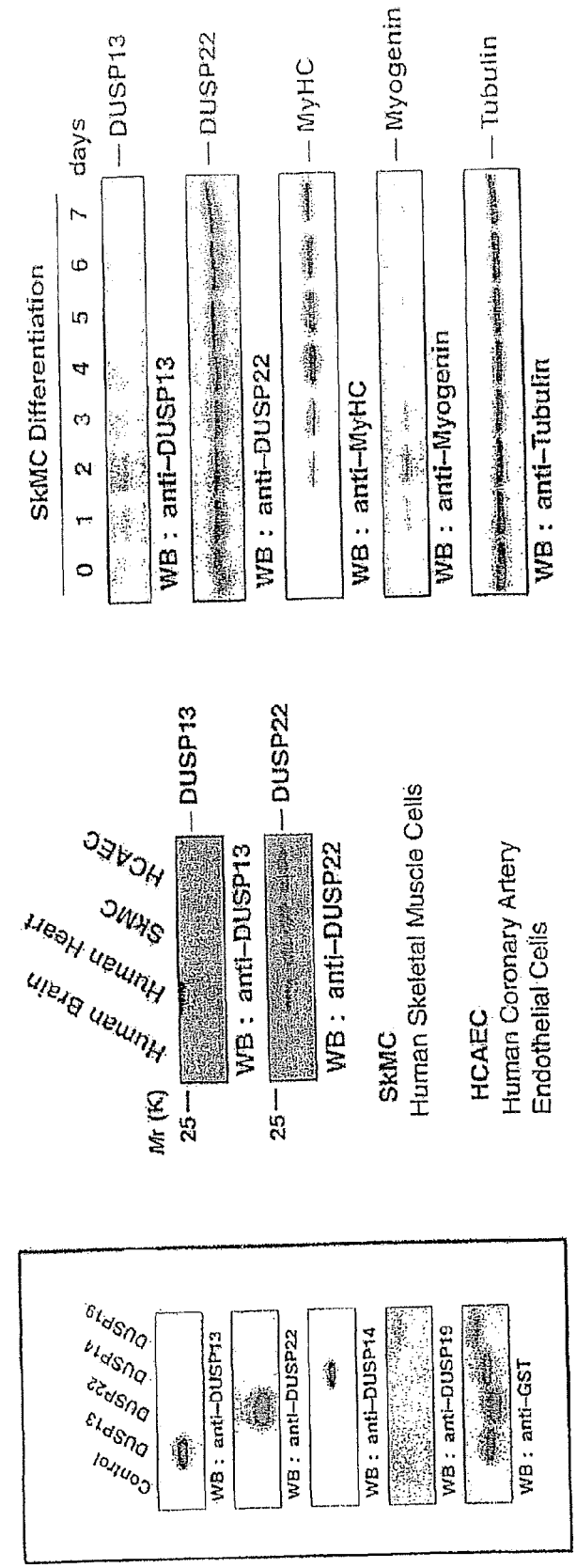
FIG. 9 shows the endogenous expression of DUSP13 at the protein level.

Next, to confirm the endogenous expression of DUSP13 at the protein level, cell extracts from human skeletal muscle satellite cell (SkMC) and human heart, in which the expression of the mRNA was observed, were subjected to SDS-polyacrylamide gel electrophoresis (SDS-PAGE), and then to western blotting using anti-DUSP13 antibody. As a result, the DUSP13 expression was detected at the predicted molecular weight of about 23 kDa while not observed in human brain and human coronary artery endothelial cells (FIG. 9, center). On the other hand, the DUSP22 expression was observed in all of the human brain, heart, skeletal muscle cells, and coronary artery endothelial cells on the same membrane by western blotting using anti-DUSP22 antibody (FIG. 9, center).

The antibody against DUSP13 (anti-DUSP13) was prepared by immunizing a rabbit with a peptide consisting of 17 amino acid residues in N terminus of hDUSP13 (see FIG. 1, left and FIG. 2, left, double underlined region) and purifying the IgG from the serum. The antibody was confirmed to specifically react with DUSP13 among each of the DSP-recombinant proteins purified after expressed in E. coli (FIG. 9, left). Further, to study the DUSP13 expression change during the muscle cell differentiation process, human skeletal muscle satellite cells, SkMCs were differentiated, and then the expression was detected at the protein level by western blotting. At the protein level, expression was increased from day 1 after the differentiation and then decreased from day 3 (FIG. 9, right, top panel), and the same results were obtained at the mRNA level.

7. Effect of DUSP13 on Cardiomyocyte Differentiation

Figure 10:
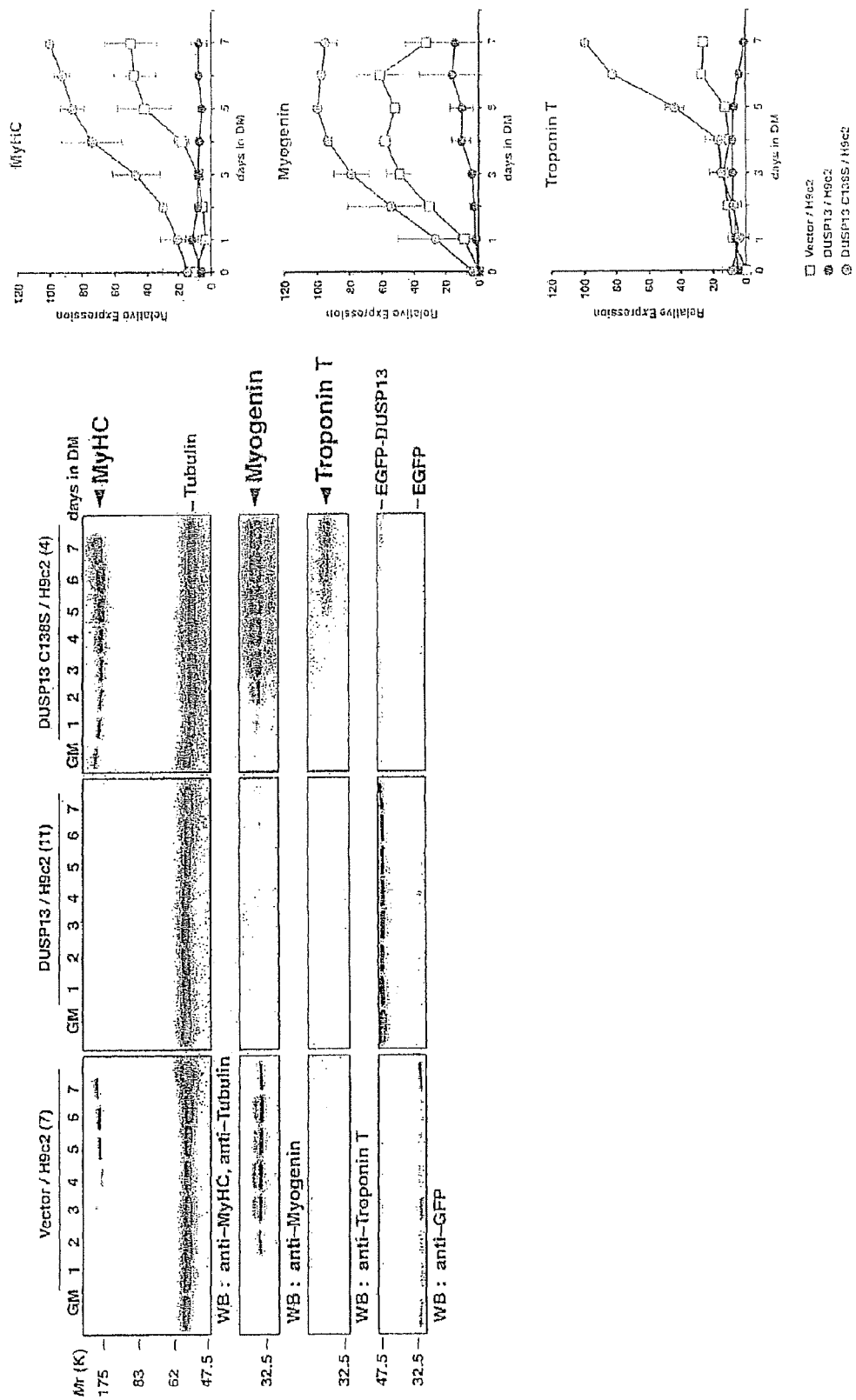
FIG. 10 shows the effect of human DUSP13 and its dominant negative enzyme human DUSP13 C138S on cardiomyocyte differentiation over time.
Figure 12:
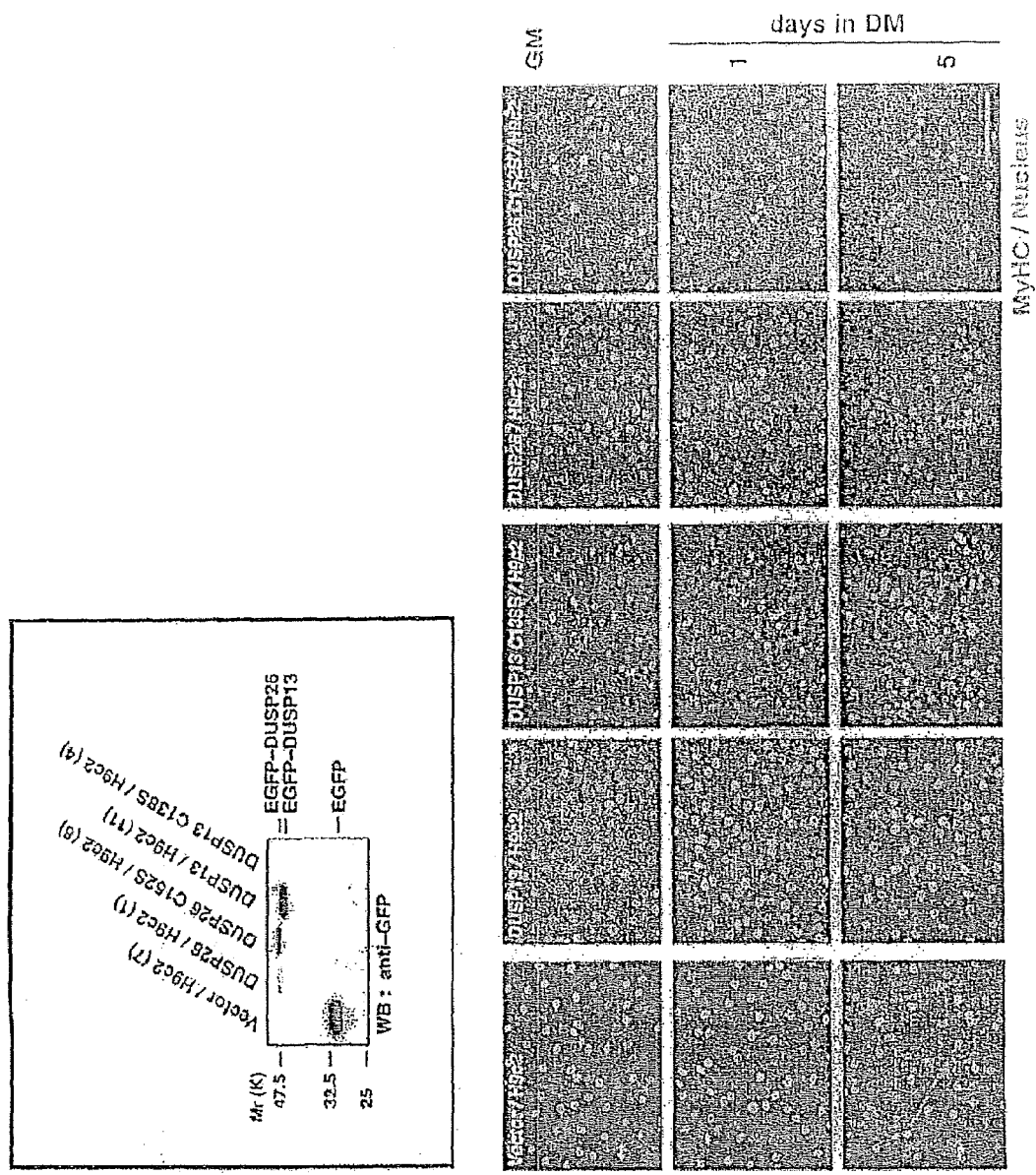
FIG. 12 shows the effect of human DUSP13, its dominant negative enzyme human DUSP13 C138S, DUSP26, and its dominant negative enzyme DUSP26 C152S on cardiomyocyte differentiation over time.
Figure 13:
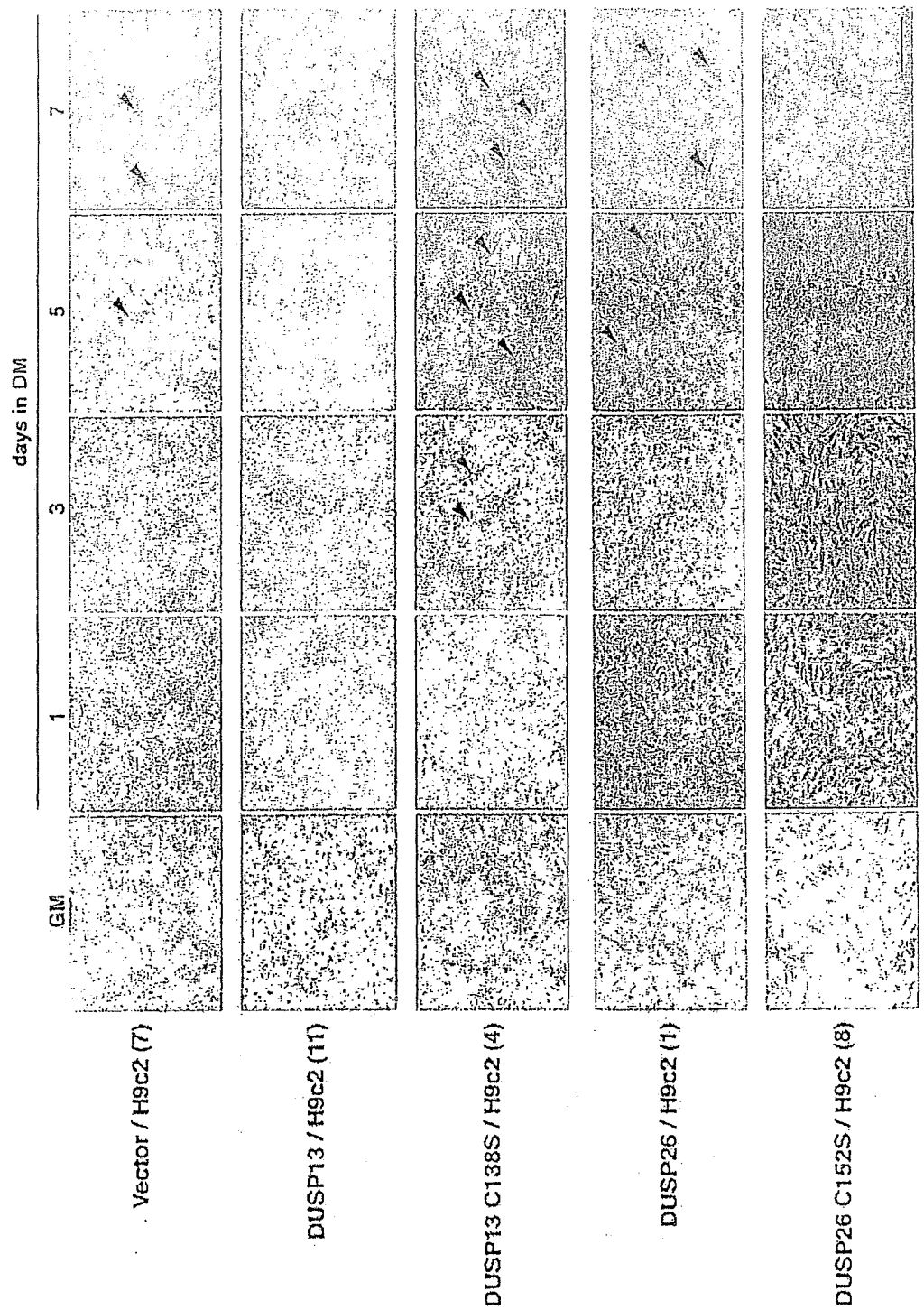
FIG. 13 shows light microscopic photographs showing the myotube formation in differentiation process.

Next, to study the physiological roles of the protein in mammalian cardiomyocytes, stably expressing cell lines of each wild-type protein and their dominant negative protein, CS mutants, were obtained together with Vector/H9c2 as a control by using rat fetal cardiomyocyte H9c2. Then, each clone was differentiated by removing serum, and the effect of each dephosphorylation enzyme on cardiomyocyte differentiation was examined by western blotting for detection of differentiation indexes (FIG. 10), cellular immunostaining (FIG. 11 and FIG. 12), and morphological observation (FIG. 13). As a result, western blotting of each differentiated cell extract showed that muscle differentiation indexes MyHC (Myosin Heavy Chain), Myogenin, and Troponin T were sequentially expressed in Vector/H9c2, while expressions of these were suppressed in DUSP13/H9c2 compared to that in Vector/H9c2 and were promoted in DUSP13 C138S/H9c2 (FIG. 10). On the other hand, in case of DUSP26, muscle differentiation indexes were expressed from the earlier time point in DUSP26/H9c2 compared to Vector/H9c2, while these were hardly expressed in DUSP26 C152S/H9c2. This suggested dual specificity phosphatases DUSP26 and DUSP13 specifically dephosphorylate a different subcellular target molecule.

Figure 11:
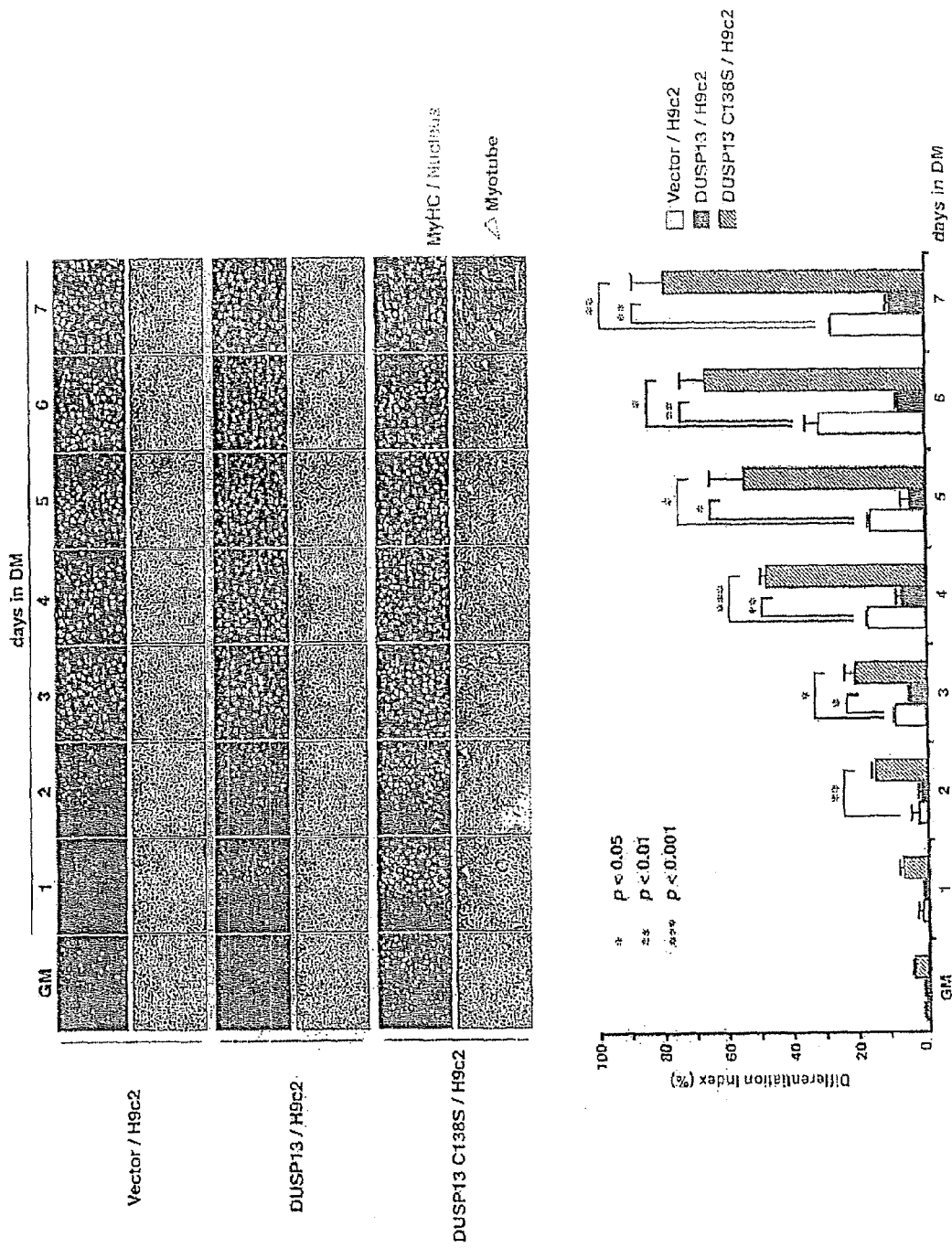
FIG. 11 shows the effect of human DUSP13 and its dominant negative enzyme human DUSP13 C138S on cardiomyocyte differentiation over time.

Next, to further confirm this result, cellular immunostaining of the above-described stably expressing cell lines was carried out over time using anti-MyHC antibody for muscle differentiation indexes MyHC and using Hoechst 33258 for nucleus, in which fluorescence image would be shown in red for MyHC and blue for nucleus. As a result, the MyHC expression was suppressed over time in DUSP13/H9c2 compared to Vector/H9c2, while this expression was promoted in DUSP13 C138S/H9c2 (FIG. 11). Further, the MyHC expression was observed from an earlier time point in DUSP26/H9c2 compared to Vector/H9c2, while the expression was hardly observed in DUSP26 C152S/H9c2 (FIG. 12). Further, the consistent results, for example the presence or absence of myotube cell formation during the differentiation process, were confirmed in morphological observation using a light microscope (see FIG. 13, tip of filled triangle).

8. Investigation of DUSP13 Substrate

Figure 14:
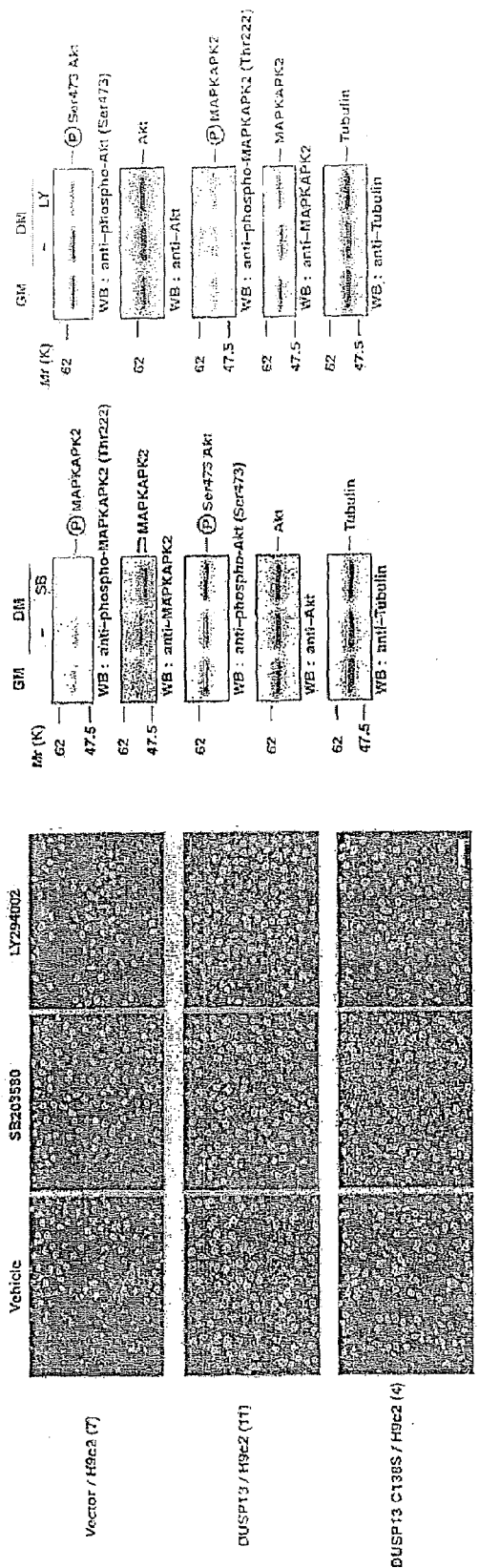
FIG. 14 shows the effect of inhibitors SB203580 and LY294002 on cardiomyocyte differentiation.

Since DUSP13 suppressed myocardial differentiation, the present inventors seeked for the target physiological substrate of DUSP13. First, it was studied whether p38MAPK pathway or PI3 kinase-Akt pathway, which were previously reported to be a differentiation signal, was involved in the differentiation of H9c2. For the generated stably expressing cell lines and their parent cell line H9c2, inhibitors of each pathway, SB203580 and LY294002, and the vehicle DMSO as a control were added to the differentiation culture medium, followed by serum removal for differentiation. As the differentiation indexes, morphological observation, cellular immunostaining (FIG. 14), and western blotting to detect the differentiation indexes were carried out as described above. As a result, both of the inhibitors suppressed the differentiation of the cell lines including the parent cell line compared to DMSO. This means that both of p38MAPK pathway and PI3 kinase-Akt pathway are necessary for the differentiation of H9c2.

Figure 15:
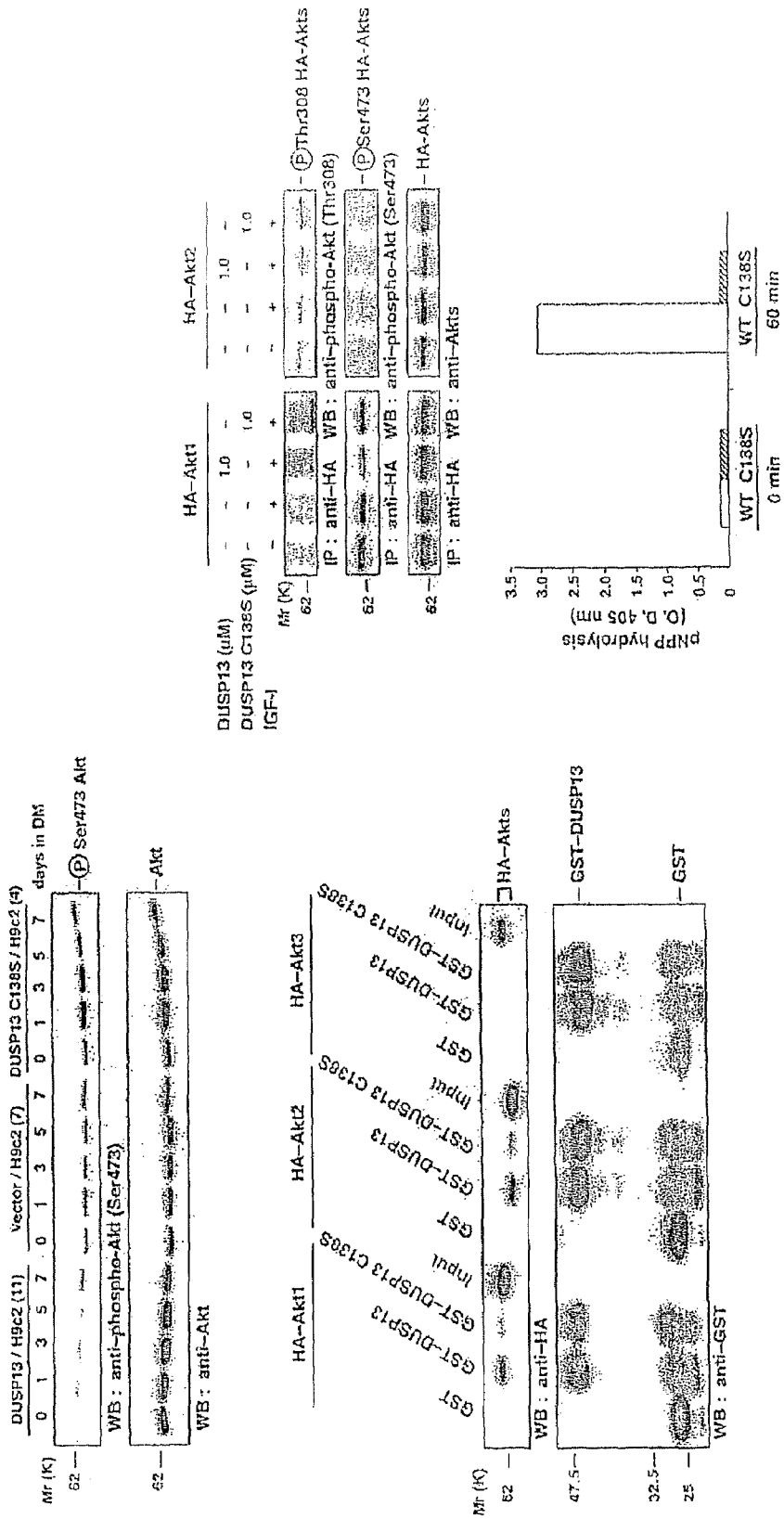
FIG. 15 shows the effect of human DUSP13 on the PI3 kinase-Akt pathway (upper left), in vitro binding between human DUSP13 protein and Akt1 or Akt2 (lower left), and dephosphorylation of these Akts by human DUSP13 protein (right).

Thus, DUSP13 was thought to suppress the pathways by dephosphorylating a signaling molecule involved in these pathways, resulting in the suppression of the differentiation. Therefore, effect of DUSP13 on signaling molecules in each pathway was examined. Accordingly, each of the stably expressing cell lines DUSP13/H9c2, Vector/H9c2, and DUSP13 C138S/H9c2 was differentiated, and cell extracts thereof were subjected to SDS-polyacrylamide gel electrophoresis (SDS-PAGE), followed by western blotting using anti-phosphorylation antibody representing the activity of each pathway. As a result, phosphorylation of Ser473 representing active form of Akt in the PI3 kinase-Akt pathway was suppressed in DUSP13/H9c2 compared to Vector/H9c2, while the phosphorylation was promoted in DUSP13 C138S/H9c2 (FIG. 15, upper left). This suggested that DUSP13 is involved in the regulation of PI3 kinase-Akt pathway, showing the possibility that DUSP13 would dephosphorylate a signaling molecule including Akt. Further, DUSP13 was shown to bind with Akt isoforms Akt1 and Akt2 in vitro (FIG. 15, lower left) and directly dephosphorylates the phosphorylated Ser-473 thereof (see FIG. 15, right, second panel from the top). Further, each of the stably expressing cell lines DUSP26/H9c2, Vector/H9c2, and DUSP26 C152S/H9c2 was differentiated, and cell extracts thereof were subjected to western blotting using anti-phosphorylated Akt (Ser473) antibody or anti-phosphorylated Akt (Thr308) antibody, which recognizes activated Akt. In both cases, the phosphorylation of Akt was promoted in DUSP26/H9c2 compared to Vector/H9c2, while suppressed in DUSP26 C152S/H9c2. This suggested that DUSP26 is also involved in the regulation of Akt pathway.

INDUSTRIAL APPLICABILITY

A protein of the present invention is a dephosphorylation enzyme that regulates cardiomyocyte differentiation or a dominant negative enzyme thereof having an activity to regulate cardiomyocyte differentiation. A protein of the present invention, a DNA encoding the protein and a recombinant vector comprising the DNA can be used as a regulator of cardiomyocyte differentiation and are also expected to be applied to a prophylactic agent and therapeutic agent for cardiomyocyte differentiation-related heart diseases. Further, a transformant into which a recombinant vector of the present invention is introduced can be used for a method of screening for a substance that promotes or suppresses cardiomyocyte differentiation by, for example, culturing the transformant in the presence of a test substance and measuring and evaluating the degree of cardiomyocyte differentiation. Further, similar screening methods are expected to be also applied to a method of screening for a potential substance for a prophylactic agent and therapeutic agent for cardiomyocyte differentiation-related heart diseases. A differentiation regulater and a substance that promotes or suppresses cardiomyocyte differentiation of the present invention are also expected to be applied to regenerative medicine of heart. Namely, in the regenerative medicine of heart, a method to induce cardiomyocyte or the like from a stem cell and efficiently transplant it into a human body is considered essential. In such circumstances, the regulater of cardiomyocyte differentiation and the substance that promotes or suppresses the cardiomyocyte differentiation of the present invention are considered to be useful for improving the efficiency of heart transplant, including more efficient preparation of cardiomyocytes for transplant and improvement in graft survival when the regenerated heart is transplanted into a patient.

The invention claimed is:

1. A method for activating promotion of cardiomyocyte differentiation comprising administering, to a cardiomyocyte, a protein consisting of any one of the following amino acid sequences (a) to (c) and having an activity of promoting cardiomyocyte differentiation, or a recombinant vector comprising a DNA sequence encoding the protein and capable of expressing the protein in a cardiomyocyte:

(a) an amino acid sequence wherein cysteine at position 138 is substituted with another amino acid in the amino acid sequence of SEQ ID NO:2;

(b) an amino acid sequence wherein cysteine at position 138 is substituted with another amino acid and one or several amino acids other than cysteine at position 138 are deleted, substituted or added in the amino acid sequence of SEQ ID NO:2, wherein a protein consisting of the amino acid sequence has an inhibitory activity against dual specificity phosphatase;
(c) an amino acid sequence having at least 90% or more identity to the amino acid sequence of SEQ ID NO:2 and having at position 138 an amino acid other than cysteine, wherein a protein consisting of the amino acid sequence has an inhibitory activity against a dual specificity phosphatase.

* * * * *